(12) United States Patent
Pulapura et al.

(10) Patent No.: US 10,980,922 B2
(45) Date of Patent: Apr. 20, 2021

(54) HEMOSTATIC DEVICES AND METHODS OF USE

(71) Applicant: MEDTRONIC, INC., Minneapolis, MN (US)

(72) Inventors: Satish Pulapura, Bridgewater, NJ (US); Fatima Buevich, Highland Park, NJ (US); Jorie S. Soskin, Edina, MN (US); Franklin R. Mansfield, Jacksonville, FL (US); Kai R. Worrell, Hopkins, MN (US); Charlie Wood, Delano, MN (US); Jorge Alberto Trevino Blanco, Minneapolis, MN (US); Narvel M. Brooks, III, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 22 days.

(21) Appl. No.: 15/583,086

(22) Filed: May 1, 2017

(65) Prior Publication Data
US 2017/0319755 A1 Nov. 9, 2017

Related U.S. Application Data

(60) Provisional application No. 62/331,209, filed on May 3, 2016.

(51) Int. Cl.
*A61L 31/16* (2006.01)
*A61L 31/04* (2006.01)
(Continued)

(52) U.S. Cl.
CPC ............ *A61L 31/16* (2013.01); *A61K 31/496* (2013.01); *A61K 31/65* (2013.01); *A61L 31/04* (2013.01);
(Continued)

(58) Field of Classification Search
CPC ................. A61N 1/059; A61L 31/08
See application file for complete search history.

(56) References Cited

U.S. PATENT DOCUMENTS

| 4,600,001 A | 7/1986 | Gilman |
| 5,800,372 A * | 9/1998 | Bell .................... A61F 13/0203 |
| | | 128/DIG. 8 |

(Continued)

FOREIGN PATENT DOCUMENTS

| CN | 102341133 A | 2/2012 |
| CN | 102834123 A | 12/2012 |

OTHER PUBLICATIONS

N. Coker, et al. "Tranexamic acid applied topically to achieve haemostasis," Anaesthesia, vol. 55, No. 6, Jun. 15, 2000, pp. 600-601.
(Continued)

*Primary Examiner* — Kami A Bosworth
*Assistant Examiner* — Leah J Swanson
(74) *Attorney, Agent, or Firm* — Sorell, Lenna & Schmidt, LLP

(57) ABSTRACT

An anchorage device is provided that is configured to surround an implantable medical device. The anchorage device includes a substrate formed from a first material and a second material. At least one of the first and second materials includes a hemostatic agent. Kits, systems and methods are disclosed.

20 Claims, 37 Drawing Sheets

(51) Int. Cl.
*A61L 31/14* (2006.01)
*A61K 31/496* (2006.01)
*A61M 37/00* (2006.01)
*A61K 31/65* (2006.01)
*A61L 31/10* (2006.01)

(52) U.S. Cl.
CPC ............ *A61L 31/042* (2013.01); *A61L 31/10* (2013.01); *A61L 31/146* (2013.01); *A61L 31/148* (2013.01); *A61M 37/00* (2013.01); *A61L 2300/406* (2013.01); *A61L 2300/418* (2013.01); *A61M 2205/0238* (2013.01)

(56) References Cited

U.S. PATENT DOCUMENTS

| | | | | |
|---|---|---|---|---|
| 8,721,519 | B2* | 5/2014 | Sheu | A61F 2/0045 600/30 |
| 8,911,765 | B2 | 12/2014 | Moses et al. | |
| 9,468,654 | B1* | 10/2016 | Razavi | A61K 9/0014 |
| 2002/0019602 | A1 | 2/2002 | Geng | |
| 2005/0113849 | A1* | 5/2005 | Popadiuk | A61L 31/146 606/151 |
| 2007/0134293 | A1* | 6/2007 | Huey | A61L 15/18 424/424 |
| 2007/0225631 | A1* | 9/2007 | Bowlin | A61K 38/363 602/52 |
| 2007/0276308 | A1 | 11/2007 | Huey et al. | |
| 2008/0138387 | A1 | 6/2008 | Machiraju | |
| 2008/0241212 | A1 | 10/2008 | Moses et al. | |
| 2012/0185004 | A1 | 7/2012 | McJames et al. | |
| 2013/0041407 | A1* | 2/2013 | Montenegro | A61L 17/08 606/231 |
| 2013/0317418 | A1* | 11/2013 | Freyman | A61L 31/06 604/24 |
| 2014/0031912 | A1 | 1/2014 | McJames et al. | |
| 2014/0343673 | A1 | 11/2014 | Matheny | |
| 2015/0086607 | A1 | 3/2015 | Johnson et al. | |

OTHER PUBLICATIONS

International Search Report of the International Searching Authority(ISA/EPO) dated Aug. 1, 2017 of International PCT Application No. PCT/US2017/030510 filed on May 2, 2017.
International Search Report of the International Searching Authority(ISA/EPO) dated Aug. 3, 2017 of International PCT Application No. PCT/US2017/030504 filed on May 2, 2017.
International Search Report of the International Searching Authority(ISA/EPO) dated Aug. 10, 2017 of International PCT Application No. PCT/US2017/030517 filed on May 2, 2017.
International Search Report of the International Searching Authority(ISA/EPO) dated Aug. 9, 2017 of International PCT Application No. PCT/US2017/030530 filed on May 2, 2017.
PCT/US2017/030513 International Preliminary Report on Patentability Chapter I mailed from WIPO dated Nov. 15, 2018 and Written Opinion of the International Searching Authority—European Patent Office.
European Patent Office Communication—Examination Report—dated Jan. 31, 2020 Application No. 17723207.1; Title: Hemostatic devices and methods of use.
European Patent Office, Patentlaan 2, 2288 EE Rijswijk, Netherlands, Communication from the Examining Division, Application No. 1772307.1 dated Nov. 17, 2020, response due within 4 months.
European Patent Office, Patentlaan 2, 2288 EE Rijswijk, Netherlands, Communication from the Examining Division, Application No. 17726393.6 dated Oct. 28, 2020, response due within 4 months.
European Patent Office, Patentlaan 2, 2288 EE Rijswijk, Netherlands, Communication from the Examining Division, Application No. 17723206.3 dated Oct. 28, 2020, response due within 4 months.
China National Intellectual Property Administration, Notice of the First Office Action, Application No. 201780027898.3, dated Dec. 29, 2020.
BMC Cardiovascular Disorders, vol. 16, Osman Beton et al., Bleeding complications during cardiac electronic device implantation in patients receiving antithrombotic therapy: is there any value of localthranexamic acid? Article No. 73.
China National Intellectual Property Administration, Application/Patent No. 201780027035.6, Notice on the First Office Action, dated Dec. 21, 2020.

* cited by examiner

| # | MATERIAL | ABSORPTION RATING | COMMENTS | |
|---|---|---|---|---|
| 1 | SURGIFOAM | 5 | FASTER THAN JELLO |  |
| 2 | CHITOSAN FILM | 1 | WITHIN 1-2 SEC |  |
| 3 | CHITOSAN + MESH | 4 | WITHIN 3 MIN |  |
| 4 | PVP + MESH | 2 | WITHIN 3 MIN |  |
| 6 | PEG + MESH | 3 | WITHIN 3 MIN |  |
| 7 | JELLO | 6 | SEVERAL HOURS |  |
| 5 | CHITOSAN + PVP + MESH | | LONGER THAN 3 MIN BUT FASTER THAN SURGIFOAM, MAY BE WAS DRYER THAN OTHER SAMPLES | |

| PREPARED SAMPLES OF ORC AND GLYCOPRENE | | | BEFORE IMMERSION | BEFORE INCUBATION | AFTER INCUBATION 48 H | AFTER INCUBATION 48 H, BUFFER DECANTED |
|---|---|---|---|---|---|---|
| GROUP 1 | SAMPLE | DESCRIPTION | | | | |
| A | 1, 2 | GLYCOPRENE & TYRC-COATED ORC |  |  |  |  |
| B | 3, 4 | TYRX-COATED GLYCOPRENE & ORC |  |  |  |  |
| C | 5, 6 | TYRX-COATED GLYCOPRENE & TYRX-COATED ORC |  |  |  |  |
| D | 9, 10 | TYRX-COATED ORC |  |  |  |  |
| E | 11, 12 | TYRX-COATED GLYCOPRENE |  |  |  |  |

EXPECTED TOTAL DRUG CONTENT OF EACH SAMPLE

| | WEIGHT (mG) | | DRUG FROM COATED ORC | | DRUG FROM COATED GLYCO | | TOTAL DRUG | |
|---|---|---|---|---|---|---|---|---|
| SAMPLE | COATED ORC | COATED GLYCOPRENE | EPI+MINO | RIF | EPI+MINO | RIF | EPI+MINO | RIF |
| 1 | 60.4 | 0 | 6633476 | 8297348 | 0 | 0 | 6633476 | 8297348 |
| 2 | 57.7 | 0 | 6336946 | 7926440 | 0 | 0 | 6336946 | 7926440 |
| 3 | 0 | 14.4 | 0 | 0 | 4009884 | 3789638 | 4009884 | 3789638 |
| 4 | 0 | 14.9 | 0 | 0 | 4149117 | 3921223 | 4149117 | 3921223 |
| 5 | 63.6 | 14.7 | 6984918 | 8736942 | 4093424 | 3868589 | 11078342 | 12605531 |
| 6 | 59.1 | 13.3 | 6490702 | 8118962 | 3703574 | 3500152 | 10194276 | 11618914 |

| 9 | 49.3 | 0 | 5414410 | 6772504 | 0 | 0 | 5414410 | 6772504 |
| 10 | 53.2 | 0 | 5842730 | 7308260 | 0 | 0 | 5842730 | 7308260 |
| 11 | 0 | 10.3 | 0 | 0 | 2868181 | 2710644 | 2868181 | 2710644 |
| 12 | 0 | 11.5 | 0 | 0 | 3202338 | 3026447 | 3202338 | 3026447 |

100% OF DRUG IN SAMPLE

"MINO" REFERS TO MINOCYCLINE, "RIF" REFERS TO RIFAMPIN AND "EPI" REFERS TO EPINEPHRINE.

FIG. 23F

ELUTION RESULTS

| GLYCOPRENE & TYRX-COATED ORC | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|
| SAMPLE | PBS VOLUME (mL) | TIME | EPI-MINO | MINO | RIF | EPI+MINO | RIF | | EPI+MINO | RIF | | EPI+MINO | RIF | | EPI+MIN | RIF | MINO | RIF |
| 1 | 0 | 0 | 0 | 0 | 0 | 0 | 0 | | 0 | 0 | | 0 | 0 | | 0% | 0% | 0% | 0% |
| | 20 | 2 | 19137 | 31015 | 14038 | 50152 | 14038 | | 1003040 | 280760 | | 1003040 | 280760 | | 15% | 3% | 16% | 4% |
| | 10 | 4 | 41620 | 51945 | 36992 | 93565 | 36992 | | 935650 | 369920 | | 1938690 | 650680 | | 29% | 8% | 30% | 8% |
| | 5 | 6 | 124225 | 140802 | 146848 | 265027 | 146848 | | 1325135 | 734240 | | 3263825 | 1384920 | | 49% | 17% | 51% | 17% |
| | 2 | 26 | 268006 | 392109 | 332954 | 660115 | 332954 | | 1320230 | 665908 | | 4584055 | 2050828 | | 69% | 25% | 70% | 25% |
| | 2 | 30 | 660873 | 839769 | 2029683 | 1500642 | 2029683 | | 3001284 | 4059366 | | 7585339 | 6110194 | | 114% | 74% | 116% | 75% |
| 2 | 0 | 0 | 0 | 0 | 0 | 0 | 0 | | 0 | 0 | | 0 | 0 | | 0% | 0% | 0% | 0% |
| | 20 | 2 | 20678 | 33248 | 14715 | 53926 | 14715 | | 1078520 | 294300 | | 1078520 | 294300 | | 17% | 4% | 16% | 4% |
| | 10 | 4 | 41300 | 50426 | 37316 | 91726 | 37316 | | 917260 | 373160 | | 1995780 | 667460 | | 31% | 8% | 30% | 8% |
| | 5 | 6 | 122306 | 138199 | 132796 | 260505 | 132796 | | 1302525 | 663980 | | 3298305 | 1331440 | | 52% | 17% | 51% | 17% |
| | 2 | 26 | 245110 | 364796 | 313035 | 609906 | 313035 | | 1219812 | 626070 | | 4518117 | 1957510 | | 71% | 25% | 70% | 25% |
| | 2 | 30 | 659566 | 828742 | 2022220 | 1488328 | 2022220 | | 2976656 | 4044440 | | 7494773 | 6001950 | | 118% | 76% | 116% | 75% |

*FIG. 23G*

ELUTION RESULTS

| TYRX-COATED GLYCOPRENE & ORC | | PEAK AREA | | | CONCENTRATION = RF*AREA | | TOTAL DRUG AT TIMEPT | | TOTAL DRUG OVER TIME | | % DRUG RELEASE OVER TIME | | | |
|---|---|---|---|---|---|---|---|---|---|---|---|---|---|---|
| SAMPLE | PBS VOLUME (mL) | TIME | EPI+MINO | MINO | RIF | EPI+MINO | RIF | EPI+MINO | RIF | EPI+MINO | RIF | EPI+MIN | RIF | MINO | RIF |
| 3 | 0 | 0 | 0 | 0 | 0 | 0 | 0 | 0 | 0 | 0 | 0 | 0% | 0% | 0% | 0% |
|  | 20 | 2 | 17879 | 41181 | 48747 | 59060 | 48747 | 1181200 | 974940 | 1181200 | 974940 | 29% | 26% | 28% | 24% |
|  | 10 | 4 | 57269 | 104342 | 143275 | 161611 | 143275 | 1616110 | 1432750 | 2797310 | 2407690 | 70% | 64% | 73% | 66% |
|  | 5 | 6 | 37587 | 52912 | 87956 | 90499 | 87956 | 452495 | 439780 | 3249805 | 2847470 | 81% | 75% | 85% | 79% |
|  | 2 | 26 | 34921 | 59446 | 69479 | 94367 | 69479 | 188734 | 138958 | 3438539 | 2986428 | 86% | 79% | 89% | 82% |
|  | 2 | 30 | 48834 | 67577 | 153374 | 116411 | 153374 | 232822 | 306748 | 3671361 | 3293176 | 92% | 87% | 96% | 91% |
| 4 | 0 | 0 | 0 | 0 | 0 | 0 | 0 | 0 | 0 | 0 | 0 | 0% | 0% |  |  |
|  | 20 | 2 | 16404 | 37152 | 43346 | 53356 | 43346 | 1071120 | 866920 | 1071120 | 866920 | 26% | 22% |  |  |
|  | 10 | 4 | 73490 | 133950 | 184024 | 207440 | 184024 | 2074400 | 1840240 | 3145520 | 2707160 | 76% | 69% |  |  |
|  | 5 | 6 | 46933 | 68490 | 114634 | 115423 | 114634 | 577115 | 573170 | 3722635 | 3280330 | 90% | 84% |  |  |
|  | 2 | 26 | 16324 | 32107 | 29531 | 48431 | 29531 | 96862 | 59062 | 3819497 | 3339392 | 92% | 85% |  |  |
|  | 2 | 30 | 67255 | 89185 | 195597 | 156440 | 195597 | 312880 | 391194 | 4132377 | 3730586 | 100% | 95% |  |  |

*FIG. 23H*

ELUTION RESULTS

| TYRX-COATED GLYCOPRENE & TYRX-COATED ORC | | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|---|
| SAMPLE | PBS VOLUME (mL) | TIME | EPI-MINO | MINO | RIF | EPI+MINO | RIF | | EPI+MINO | RIF | | EPI+MINO | RIF | | EPI+MIN | RIF | MINO | RIF |
| 5 | 0 | 0 | 0 | 0 | 0 | 0 | 0 | | 0 | 0 | | 0 | 0 | | 0% | 0% | 0% | 0% |
|  | 20 | 2 | 35510 | 69016 | 57751 | 104526 | 57751 | | 2090520 | 1155020 | | 2090520 | 1155020 | | 19% | 9% | 24% | 11% |
|  | 10 | 4 | 85401 | 133154 | 146594 | 218555 | 146594 | | 2185550 | 1465940 | | 4276070 | 2620960 | | 39% | 21% | 45% | 24% |
|  | 5 | 6 | 166903 | 210876 | 225697 | 377779 | 225697 | | 1888895 | 1128485 | | 6164965 | 3749445 | | 56% | 30% | 64% | 34% |
|  | 2 | 26 | 107557 | 223674 | 142872 | 331231 | 142872 | | 662462 | 285744 | | 6827427 | 4035189 | | 62% | 32% | 81% | 44% |
|  | 2 | 30 | 904673 | 1136696 | 2179775 | 2041369 | 2179775 | | 4082738 | 4359550 | | 10910165 | 8394739 | | 98% | 67% | 109% | 74% |
| 6 | 0 | 0 | 0 | 0 | 0 | 0 | 0 | | 0 | 0 | | 0 | 0 | | 0% | 0% | | |
|  | 20 | 2 | 51925 | 93395 | 73989 | 145320 | 73989 | | 2906400 | 1479780 | | 2906400 | 1479780 | | 29% | 13% | | |
|  | 10 | 4 | 93036 | 143471 | 161113 | 236507 | 161113 | | 2365070 | 1611130 | | 5271470 | 3090910 | | 52% | 27% | | |
|  | 5 | 6 | 190265 | 231814 | 283505 | 422079 | 283505 | | 2110395 | 1417525 | | 7381865 | 4508435 | | 72% | 39% | | |
|  | 2 | 26 | 572850 | 821904 | 951334 | 1394754 | 951334 | | 2789508 | 1902668 | | 10171373 | 6411103 | | 100% | 55% | | |
|  | 2 | 30 | 451012 | 584713 | 1576514 | 1035725 | 1576514 | | 2071450 | 3153028 | | 12242823 | 9564131 | | 120% | 82% | | |

FIG. 23I

ELUTION RESULTS

| | TYRX-COATED ORC | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|---|
| SAMPLE | PBS VOLUME (mL) | TIME | EPI-MINO | MINO | RIF | EPI+MINO | RIF | | EPI+MINO | RIF | | EPI+MINO | RIF | | EPI+MIN | RIF | MINO | RIF |
| 9 | 0 | 0 | 0 | 0 | 0 | 0 | 0 | | 0 | 0 | | 0 | 0 | | 0% | 0% | 0% | 0% |
| | 20 | 2 | 15474 | 24188 | 11774 | 39633 | 11774 | | 793240 | 235480 | | 793240 | 235480 | | 15% | 3% | 15% | 3% |
| | 10 | 4 | 42228 | 52553 | 41925 | 94781 | 41925 | | 947810 | 419250 | | 1741050 | 654730 | | 32% | 10% | 30% | 8% |
| | 5 | 6 | 157128 | 175633 | 255303 | 332761 | 255303 | | 1663805 | 1276515 | | 3404855 | 1931245 | | 63% | 29% | 54% | 22% |
| | 2 | 26 | 576200 | 777329 | 1432680 | 1353529 | 1432680 | | 2707058 | 2865360 | | 6773881 | 4796605 | | 113% | 71% | 88% | 47% |
| | 2 | 30 | 148018 | 182966 | 445777 | 330984 | 445777 | | 661968 | 891554 | | 5688159 | 117% | | 125% | 84% | 117% | 77% |
| 10 | 0 | 0 | 0 | 0 | 0 | 0 | 0 | | 0 | 0 | | 0 | 0 | | 0% | 0% | | |
| | 20 | 2 | 16720 | 26959 | 12519 | 43679 | 12519 | | 873580 | 250380 | | 873580 | 250380 | | 15% | 3% | | |
| | 10 | 4 | 31732 | 40584 | 27785 | 72316 | 27785 | | 723160 | 277850 | | 1596740 | 528230 | | 27% | 7% | | |
| | 5 | 6 | 100818 | 117072 | 130127 | 217890 | 130127 | | 1089450 | 650635 | | 2686190 | 1178865 | | 46% | 16% | | |
| | 2 | 26 | 181500 | 293105 | 259567 | 474605 | 259567 | | 949210 | 519134 | | 3635400 | 1697999 | | 62% | 23% | | |
| | 2 | 30 | 612622 | 758657 | 1721196 | 1371279 | 1721196 | | 2742558 | 3442392 | | 6377958 | 5140391 | | 109% | 70% | | |

FIG. 23J

| TYRX-COATED GLYCOPRENE | | | PEAK AREA | | | CONCENTRATION = RF*AREA | | | TOTAL DRUG AT TIMEPT | | | TOTAL DRUG OVER TIME | | | % DRUG RELEASE OVER TIME | | |
|---|---|---|---|---|---|---|---|---|---|---|---|---|---|---|---|---|---|
| SAMPLE | PBS VOLUME (mL) | TIME | EPI-MINO | MINO | RIF | EPI+MINO | RIF | | EPI+MINO | RIF | | EPI+MINO | RIF | | EPI+MIN | RIF | MINO | RIF |
| 11 | 0 | 0 | 0 | 0 | 0 | 0 | 0 | | 0 | 0 | | 0 | 0 | | 0% | 0% | 0% | 0% |
| | 20 | 2 | 40576 | 86595 | 96710 | 127171 | 96710 | | 2543420 | 1934200 | | 2543420 | 1934200 | | 89% | 67% | 87% | 68% |
| | 10 | 4 | 11973 | 15530 | 25453 | 2703 | 25453 | | 275030 | 254530 | | 2818450 | 2188730 | | 98% | 76% | 96% | 77% |
| | 5 | 6 | 10658 | 9532 | 12388 | 20190 | 12388 | | 100950 | 61940 | | 2919400 | 2250670 | | 102% | 78% | 99% | 79% |
| | 2 | 26 | 7704 | 8470 | 10293 | 16174 | 10293 | | 32348 | 20586 | | 2951748 | 2271256 | | 103% | 79% | 100% | 79% |
| | 2 | 30 | 3658 | 4063 | 13183 | 7721 | 13183 | | 15442 | 26366 | | 2967190 | 2297622 | | 103% | 80% | 100% | 80% |
| 12 | 0 | 0 | 0 | 0 | 0 | 0 | 0 | | 0 | 0 | | 0 | 0 | | 0% | 0% | | |
| | 20 | 2 | 42855 | 92896 | 104242 | 135751 | 104242 | | 2715020 | 2084840 | | 2715020 | 2084840 | | 85% | 69% | | |
| | 10 | 4 | 12340 | 16191 | 28143 | 28531 | 28143 | | 285310 | 281430 | | 300330 | 2366270 | | 94% | 78% | | |
| | 5 | 6 | 9649 | 6794 | 8955 | 16443 | 8955 | | 82215 | 44775 | | 3082545 | 2411045 | | 96% | 80% | | |
| | 2 | 26 | 5532 | 4105 | 0 | 9637 | 0 | | 19274 | 0 | | 3101819 | 2411045 | | 97% | 80% | | |
| | 2 | 30 | 0 | 0 | 0 | 0 | 0 | | 0 | 0 | | 3101819 | 2411045 | | 97% | 80% | | |

*FIG. 23K*

HEMOSTATIC DEVICES AND METHODS OF USE

TECHNICAL FIELD

The present disclosure generally relates to anchorage devices and methods configured for anchoring an implantable medical device within a body, wherein the anchorage device comprises at least one hemostatic agent that is configured to elute over time.

BACKGROUND

Some known anchorage devices may be used to secure an implantable medical device within a body of a patient. The anchorage device and implantable medical device can be inserted into a desired location within the body of the patient. The anchorage device can be used to help anchor or support the implantable medical device to surrounding tissue. Some known anchorage devices are used to provide temporary support to tissue during a healing process. For example, some known anchorage devices can secure one portion of tissue to another portion of tissue. It would be desirable to stop or reduce the flow of blood at a surgical site and/or speed up the blood clotting process while anchoring the implantable medical device to tissue. This disclosure describes an improvement over these prior art technologies.

SUMMARY

New anchorage devices and methods are provided to help anchor or support an implantable medical device to surrounding tissue. In one embodiment, an anchorage device is provided that includes a substrate formed from a first material and a second material. At least one of the first and second materials includes a hemostatic agent.

In some embodiments, the first and second materials are filaments, fibers, threads or strands. The filaments, fibers, threads or strands are manipulated to form the substrate. In some embodiments, the filaments, fibers, threads or strands are woven to form the substrate. In some embodiments, the filaments, fibers, threads or strands are knitted to form the substrate. In some embodiments, the filaments, fibers, threads or strands are braided to form the substrate. In some embodiments, the filaments, fibers, threads or strands are extruded to form the substrate. In some embodiments, the filaments, fibers, threads or strands are printed, using a 3D printer, for example, to form the substrate.

In some embodiments, the substrate is a mesh. In some embodiments, the substrate is a thin walled structure, such as, for example, a wafer, sheet or tissue. The mesh and the thin walled structure are each made from the first material and the second material. That is, the filaments, fibers, threads or strands of the first and second materials are manipulated to make the mesh or the thin walled structure. For example, the filaments, fibers, threads or strands of the first and second materials may be woven, knitted, braided, extruded, or printed to make the mesh or the thin walled structure.

In some embodiments, the filaments, fibers, threads or strands of the first material and/or the filaments, fibers, threads or strands of the second material include the hemostatic agent. In some embodiments, the filaments, fibers, threads or strands of the first material and/or the filaments, fibers, threads or strands of the second material are made from the hemostatic agent. In some embodiments, the filaments, fibers, threads or strands of the first material and/or the filaments, fibers, threads or strands of the second material are coated with the hemostatic agent.

In some embodiments, the substrate includes an active pharmaceutical ingredient. In some embodiments, the active pharmaceutical ingredient is applied directly to the substrate. In some embodiments, the active pharmaceutical ingredient is applied to the substrate by coating, washing the substrate with the active pharmaceutical ingredient, or printing the active pharmaceutical ingredient onto the substrate using a 3D printer, for example.

In some embodiments, at least one of the first and second materials includes the active pharmaceutical ingredient. In some embodiments, the filaments, fibers, threads or strands of the first material include the hemostatic agent and the filaments, fibers, threads or strands of the second material include the active pharmaceutical ingredient. In some embodiments, the first and second materials are the same material and the filaments, fibers, threads or strands of the first material are coated with the hemostatic agent and the filaments, fibers, threads or strands of the second material are coated with the active pharmaceutical ingredient. In some embodiments, the filaments, fibers, threads or strands of the first material and/or the second material are made from the hemostatic agent and the filaments, fibers, threads or strands of the first material and/or the second material are coated with the active pharmaceutical ingredient.

In some embodiments, the substrate is a sheet, such as, for example, a planar sheet. In some embodiments, the substrate comprises a first piece and a second piece that is joined with the first piece. In some embodiments, the first and second pieces form an envelope, pouch, or pocket, wherein one side of the envelope, pouch, or pocket includes an opening to allow a device, such as, for example, the implantable medical device to be inserted through the opening and into a cavity of the envelope, pouch, or pocket.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which:

FIG. 23F is a table showing the expected drug content of Samples 1-6 and 9-12 in Example 13;

FIG. 23G is a table showing elution results for Samples 1-6 in Example 13;

FIG. 23H is a table showing elution results for Samples 9-12 in Example 13;

FIG. 23I is a table showing elution results for Samples 9-12 in Example 13;

FIG. 23J is a table showing elution results for Samples 9-12 in Example 13;

FIG. 23K is a table showing elution results for Samples 9-12 in Example 13;

DETAILED DESCRIPTION

Figure 1:
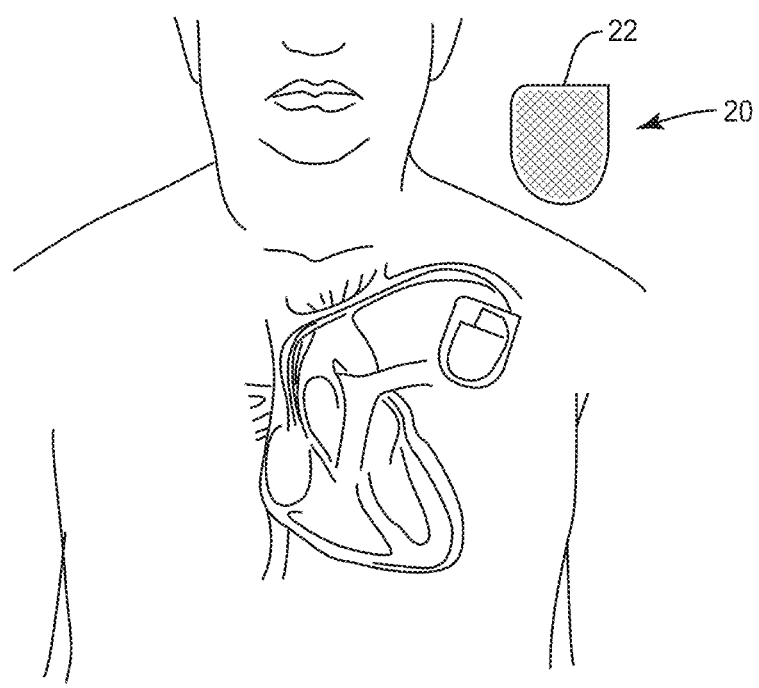
FIG. 1 is a side view of one embodiment of an anchorage device in accordance with the principles of the present disclosure.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

This disclosure is directed to anchorage devices, such as, for example, an anchorage device 20. In some embodiments, the components of anchorage device 20 can be fabricated from biologically acceptable materials suitable for medical applications, including metals, synthetic polymers, allografts, xenografts, isografts, ceramics and bone material and/or their composites, depending on the particular application and/or preference of a medical practitioner. For example, the components of anchorage device 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, tyrosine polyarylate, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polylactide, polyglycolide, polytyrosine carbonate, polycaroplactone and their combinations.

Various components of anchorage device 20 may have material composites, including the above materials, to achieve various desired characteristics such as strength, rigidity, elasticity, compliance, biomechanical performance, durability and radiolucency or imaging preference. The components of anchorage device 20, individually or collectively, may also be fabricated from a heterogeneous material such as a combination of two or more of the above-described materials. The components of anchorage device 20 may be monolithically formed, integrally connected or include fastening elements and/or instruments, as described herein.

Substrate

Anchorage device 20 includes a substrate, such as, for example, substrate 22. Substrate 22 is configured to be coupled to and/or applied to a device, such as, for example, an implantable medical device or a non-implantable medical device, as discussed herein. In some embodiments, substrate 22 is configured to surround and/or enclose at least a portion of the implantable medical device, as discussed herein. Substrate 22 is configured to be secured to tissue to support the implantable medical device at a treatment site. Implantable medical devices include, for example, vascular devices such as grafts (e.g., abdominal aortic aneurysm grafts, etc.), stents, catheters (including arterial, intravenous, blood pressure, stent graft, etc.), valves (e.g., polymeric or carbon mechanical valves,), embolic protection filters (including distal protection devices), vena cava filters, aneurysm exclusion devices, artificial hearts, cardiac jackets, and heart assist devices (including left ventricle assist devices), implantable defibrillators, subcutaneous implantable defibrillators, implantable monitors, for example, implantable cardiac monitors, electrostimulation devices and leads (including pacemakers, lead adapters and lead connectors), implanted medical device power supplies, peripheral cardiovascular devices, atrial septal defect closures, left atrial appendage filters, valve annuloplasty devices, mitral valve repair devices, vascular intervention devices, ventricular assist pumps, and vascular access devices (including parenteral feeding catheters, vascular access ports, central venous access catheters).

Implantable medical devices may also include, for example, surgical devices such as sutures of all types, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps. Implantable medical devices may also include, for example, orthopedic devices such as joint implants, acetabular cups, patellar buttons, bone repair/augmentation devices, spinal devices (e.g., vertebral disks and the like), bone pins, cartilage repair devices, and artificial tendons. Implantable medical devices may also include, for example, dental devices such as dental implants and dental fracture repair devices. Implantable medical devices may also include, for example, drug delivery devices such as drug delivery pumps, implanted drug infusion tubes, drug infusion catheters, and intravitreal drug delivery devices. Implantable medical devices may also include, for example, ophthalmic devices such as scleral buckles and sponges, glaucoma drain shunts and intraocular lenses.

Implantable medical devices may also include, for example, urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices. Implantable medical devices may also include, for example, synthetic prostheses such as breast prostheses and artificial organs (e.g., pancreas, liver, lungs, heart, etc.). Implantable medical devices may also include, for example, respiratory devices including lung catheters. Implantable medical devices may also include, for example, neurological devices such as neurostimulators, neurological catheters, neurovascular balloon catheters, neuro-aneurysm treatment coils, and neuropatches, splints, ear wicks, ear drainage tubes, tympanostomy vent tubes, otological strips, laryngectomy tubes, esophageal tubes, esophageal stents, laryngeal stents, salivary bypass tubes, and tracheostomy tubes. Implantable medical devices may also include, for example, oncological implants. Implantable medical devices may also include, for example, pain management implants In some embodiments, substrate 22 is configured to be coupled to and/or applied to or to surround and/or enclose at least a portion of a non-implantable medical device, as discussed herein. Non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

Substrate 22 can have a variety of different configurations, shapes and sizes. For example, substrate 22 can be provided with a size and shape or other configuration that can provide the functionality of supporting and immobilizing the implantable medical device at a treatment site within a patient's body, while also improving the removability of anchorage device 20 after the treatment has been completed. In some embodiments, the implantable medical device can be disposed within a pocket defined by substrate 22 and anchorage device 20 can be implanted and secured to tissue at a desired treatment site within a body of a patient. As discussed herein, during implantation, scar tissue can form at the treatment site and/or tissue can become ingrown within substrate 22. After the treatment is completed, the implantable medical device can remain in the patient as discussed below or can be removed from the patient leaving anchorage device 20 implanted. To remove anchorage device 20, tissue that is ingrown within substrate 22 can be cut or otherwise detached from substrate 22. In some embodiments, a portion of anchorage device 20 may not be removable from the tissue and will remain implanted within the patient.

Substrate 22 may be formed with one or more biocompatible materials, which may be synthetic or naturally occurring. In some embodiments, the one or more biocompatible materials include, for example, polypropylene, polyester, polytetrafluoroethylene, polyamides, silicones, polysulfones, metals, alloys, titanium, stainless steel, shape memory metals (e.g. Nitinol), and/or combinations thereof.

In some embodiments, substrate 22 is configured to be implanted temporarily within a body of a patient and/or is configured to be removed (e.g., explanted) from the patient's body after a period of time. In such embodiments, substrate 22 may include a non-biodegradable material and/or a non-bioresorbable material. For example, substrate 22 may be made entirely from a non-biodegradable material and/or a non-bioresorbable material such that substrate 22 is made only from the non-biodegradable material and/or non-bioresorbable material. In some embodiments, substrate 22 may include one or more non-biodegradable and/or a non-bioresorbable material and one or more biodegradable and/or resorbable material. In some embodiments, one side of substrate 22 may include one or more non-biodegradable and/or a non-bioresorbable material and another side of substrate 22 can include one or more biodegradable and/or resorbable material.

As used herein, the term "biodegradable" refers to, for example, a material that can be at least partially broken down or degraded by a bodily fluid and discarded as waste from the body and/or a material that can be broken down or degraded by a living organism. Thus, "non-biodegradable" can refer to a material that cannot be broken down or degraded by a bodily fluid and/or cannot be broken down or degraded by a living organism. As used herein the term "resorbable" refers to, for example, a material that can be at least partially broken down or degraded by a bodily fluid and assimilated within the body. Thus, a "non-resorbable" material as used herein can refer to, for example, a material that cannot be broken down or degraded by bodily fluid and assimilated within the body.

In some embodiments, the biocompatible biodegradable and/or bioresorbable material or materials may include polymeric and/or non-polymeric materials, such as, for example, one or more poly (alpha-hydroxy acids), poly (lactide-co-glycolide) (PLGA), polylactide (PLA), poly(L-lactide), polyglycolide (PG), polyethylene glycol (PEG) conjugates of poly (alpha-hydroxy acids), polyorthoesters (POE), polyaspirins, polyphosphazenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, tyrosine polyarylates, polyetheretherketone, polymethylmethacrylate, silicone, hyaluronic acid, chitosan, or combinations thereof. In one embodiment, substrate 22 comprises Glycoprene, which is sold by Poly-Med, Inc. As used herein, the term "glycoprene" or "Glycoprene" refers to Glycoprene® or Glycoprene II®. Glycoprene® can refer to different variations of the material sold under the trade name Glycoprene®, such as, for example, Glycoprene®6829, Glycoprene® 8609 and Glycoprene® 7027.

In some embodiments, the biocompatible non-biodegradable and/or non-bioresorbable material or materials may include polymeric and/or non-polymeric materials, such as, for example, polyurethane, polyester, polytetrafluoroethylene (PTFE), polyethylacrylate/polymethylmethacrylate, polylactide, polylactide-co-glycolide, polyamides, polydioxanone, polyvinyl chloride, polymeric or silicone rubber, collagen, thermoplastics, or combinations thereof.

In some embodiments, substrate 22 is configured to be permanently implanted within a body of a patient. In such embodiments, substrate 22 may include a biodegradable material and/or a bioresorbable material. For example, substrate 22 may be made entirely from a biodegradable material and/or a bioresorbable material such that substrate 22 is made only from the biodegradable material and/or bioresorbable material.

Figure 5:
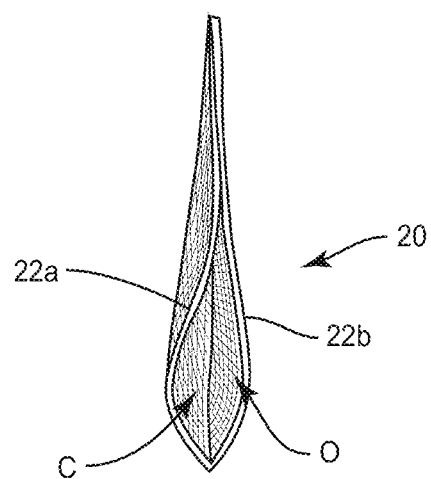
FIG. 5 is a perspective view of one embodiment of the anchorage device shown in FIG. 4.
Figure 6:
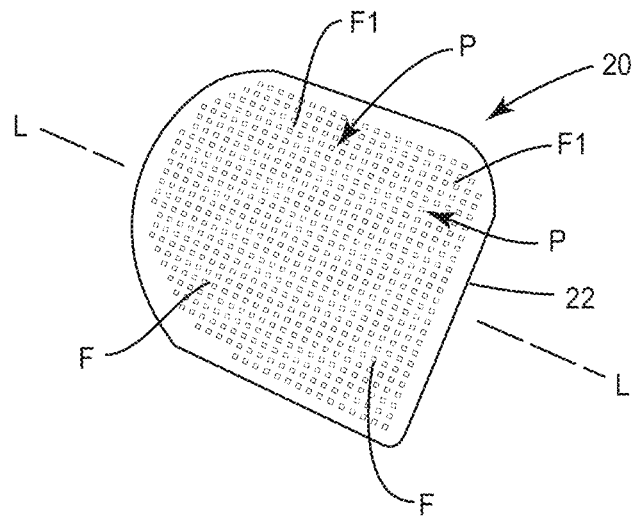
FIG. 6 is a perspective view of one embodiment of the anchorage device shown in FIG. 1 in accordance with the principles of the present disclosure.
Figure 7:
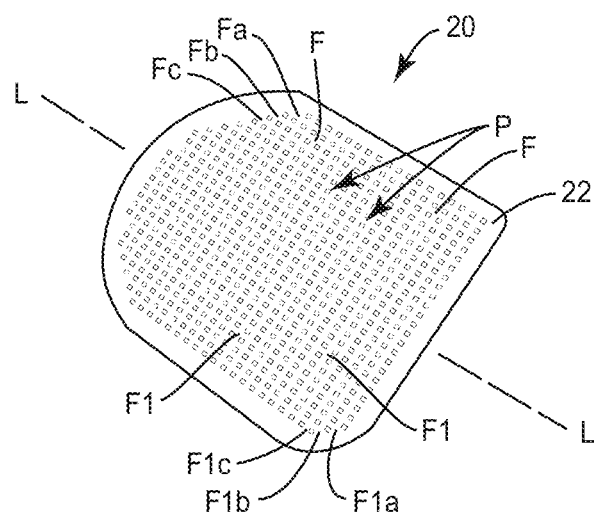
FIG. 7 is a perspective view of one embodiment of the anchorage device shown in FIG. 6.
Figure 8:
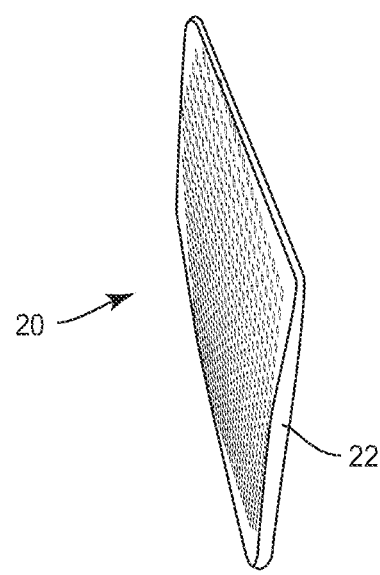
FIG. 8 is a perspective view of one embodiment of the anchorage device shown in FIG. 6.
Figure 9:
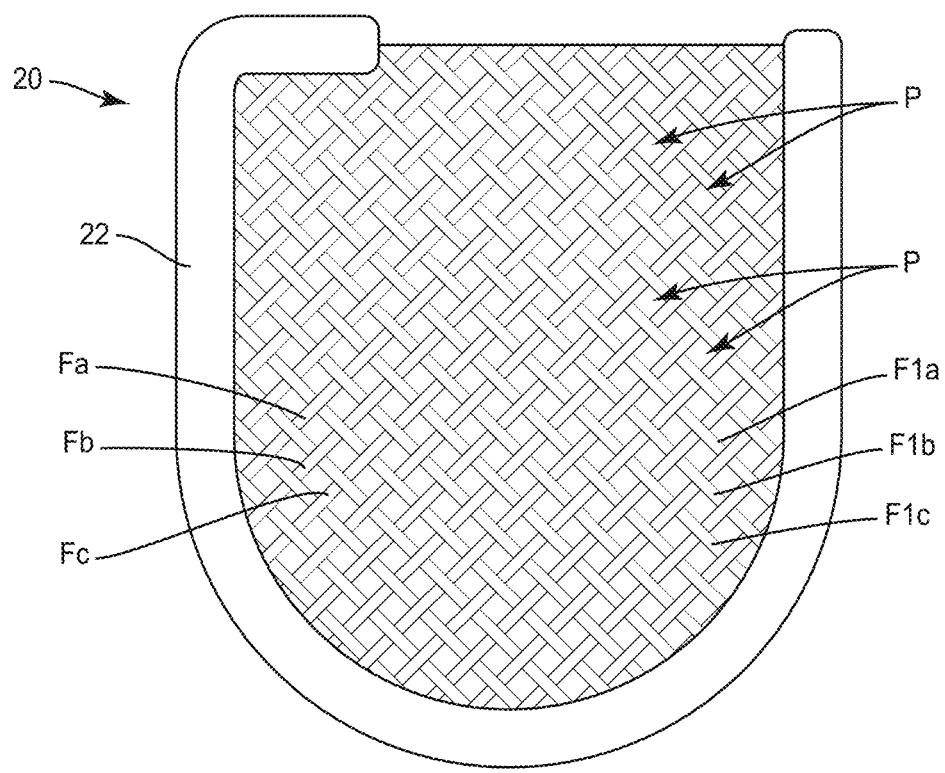
FIG. 9 is a perspective, close-up view of a portion of one embodiment of the anchorage device shown in FIG. 1 in accordance with the principles of the present disclosure.

In some embodiments, substrate 22 is provided in the form of a mesh, as shown in FIGS. 1-13. In some embodiments, the mesh is web or fabric with a construction of knitted, braided, woven or non-woven filaments or fibers F that are interlocked in such a way to create a fabric or a fabric-like material that includes a matrix of filaments F that define multiple pores P, as shown in FIGS. 6 and 7, for example. That is, the space between adjacent filaments or fibers F define pores P of the mesh. Pores P may be beneficial to allow tissue in-growth, for example. In some embodiments, apertures may be formed in the mesh by cutting the filaments or fibers F to decrease the areal density (e.g., surface density) or mass of the mesh and/or further facilitate tissue in-growth. In some embodiments, the apertures that extend through the filaments or fibers F are larger than pores P defined by the filaments or fibers F.

In some embodiments, substrate 22 is provided in the form of a thin walled structure, such as, for example, a wafer, sheet or tissue. In some embodiments, the thin walled structure does not include any pores or apertures, in contrast to the mesh discussed herein. In some embodiments, the thin walled structure is web or fabric with a construction of knitted, braided, woven or non-woven filaments or fibers, such as, for example, filaments or fibers F that are interlocked in such a way to create a fabric or a fabric-like material that includes a matrix of filaments or fibers F. In some embodiments, the thin walled structure includes pores or apertures that are smaller than the pores or apertures of the mesh discussed herein. In some embodiments, the thin walled structure has a thickness that is less than a thickness of the mesh discussed herein. In some embodiments, the thickness of the thin walled structure is between about 0.001 inches and about 0.1 inches.

In some embodiments, substrate 22 is a mesh that includes a plurality of fibers F that extend parallel to a longitudinal axis L defined by substrate 22 and a plurality of fibers F1 that extends transverse to longitudinal axis L, as shown in FIGS. 4-8. In some embodiments, fibers F and/or fibers F1 may be disposed at alternate orientations, relative to longitudinal axis L, such as, for example, transverse, perpendicular, parallel and/or other angular orientations such as acute or obtuse, co-axial and/or may be offset or staggered.

Figure 4:
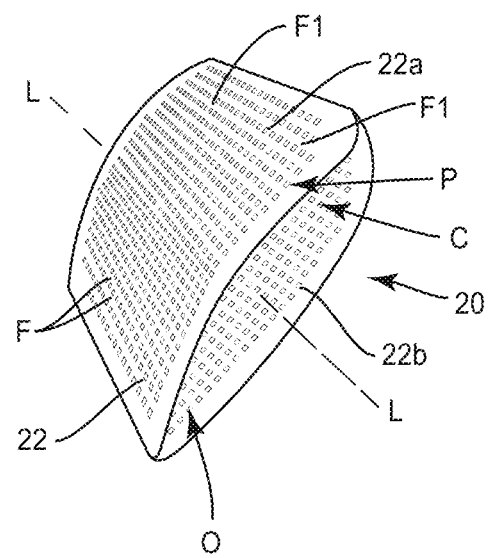
FIG. 4 is a perspective view of one embodiment of the anchorage device shown in FIG. 1 in accordance with the principles of the present disclosure.

In some embodiments, substrate 22 is a pocket or envelope in which an implantable medical device can be at least partially disposed. That is, substrate 22 is a pouch, bag, covering, shell, or receptacle. For example, substrate 22 can include a first piece 22a and a second piece 22b that is joined with first piece 22a, as shown in FIGS. 4 and 5. First and second pieces 22a, 22b are joined to form the pocket or envelope. In some embodiments, first and second pieces 22a, 22b are joined along three sides of the pocket or envelope to form a cavity C, as shown in FIG. 4, for example. First and second pieces 22a, 22b are not joined at a fourth side of the pocket or envelope to define an opening O such that an implantable medical device can be inserted through opening O and into cavity C to enclose, encase or surround all or a portion of the implantable medical device within cavity C. In some embodiments, first and second pieces 22a, 22b are joined with one another along three sides of the pocket or envelope by heat, ultrasonically, bonding, knitting, or adhesive. In some embodiment, the pocket or envelope is monolithically formed by molding the pocket or envelope or producing the pocket or envelope by 3D printing, for example.

Figure 14:
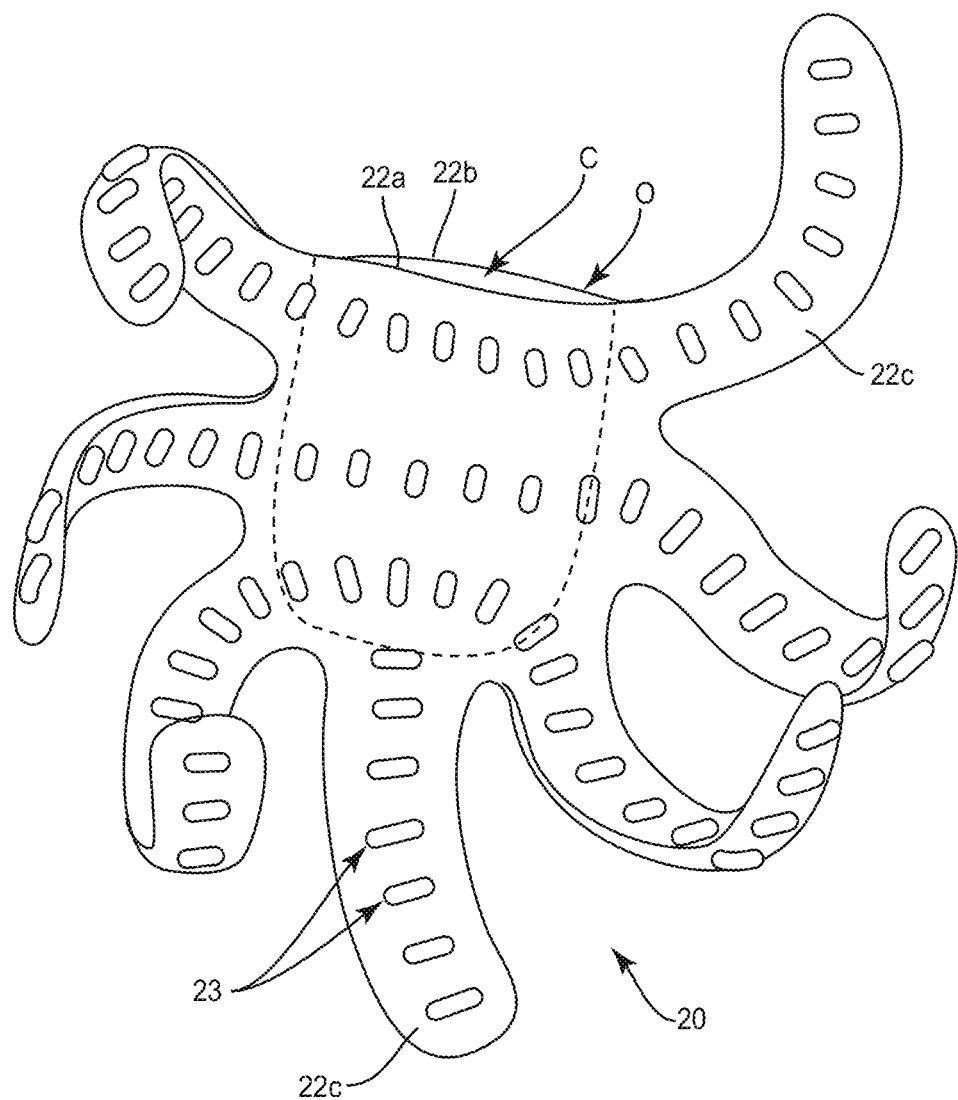
FIG. 14 is a perspective view of an anchorage device in accordance with the principles of the present disclosure.
Figure 15:
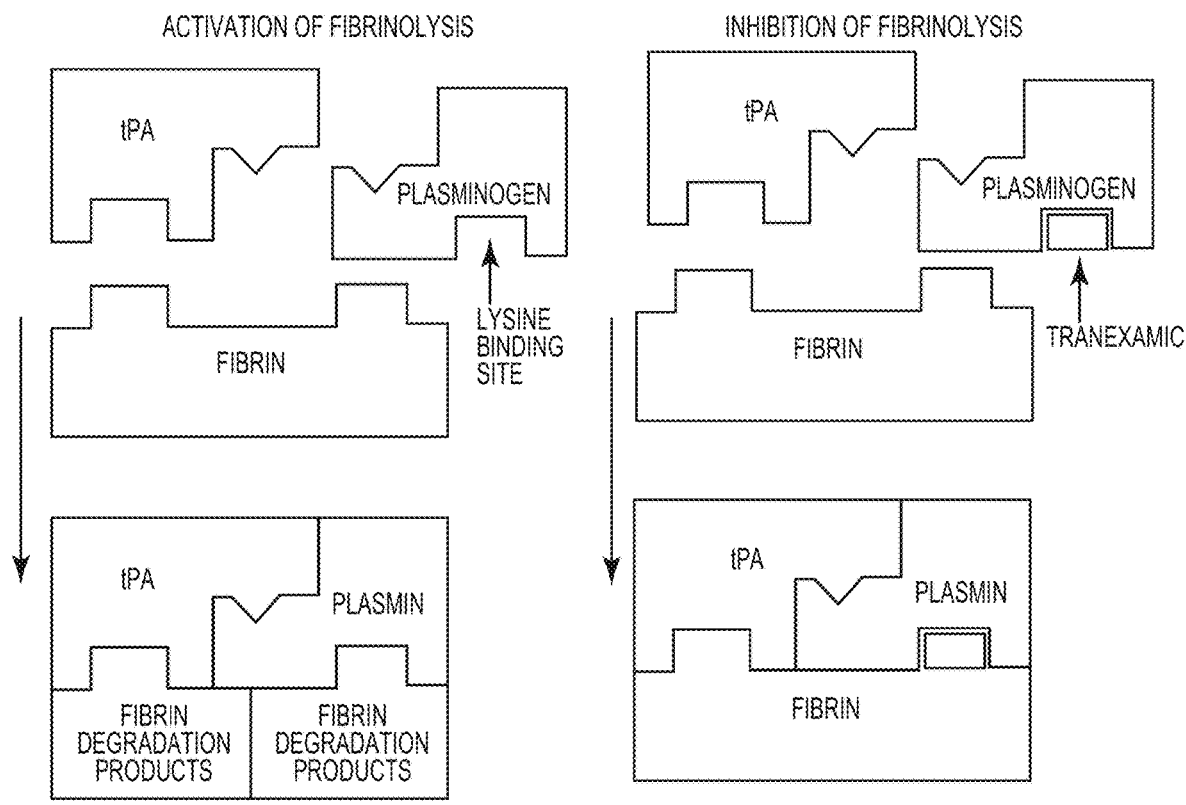
FIG. 15 is a depiction of the mechanism of action for a hemostatic agent in accordance with the principles of the present disclosure.

In some embodiments, anchorage device 20 includes one or a plurality of arms, such as, for example, extensions 22c that extend outwardly from the pocket formed by first and second pieces 22a, 22b, as shown in FIG. 14. In some embodiments, extensions 22c are spaced apart from one another and/or are positioned radially about the pocket. In some embodiments, at least one of extensions 22c includes one or a plurality of openings 23 that extends through a thickness of extension 22c. Openings 23 are spaced apart along a length of extension 23. In some embodiments, openings 23 each have the same width or diameter. In some embodiments, openings 23 each have an oval or oblong shape. Extensions 22c are configured to be coupled to tissue when anchorage device 20 is inserted into an area, such as, for example, a body cavity to secure an implantable medical device within the pocket to the body. In some embodiments, at least one of extensions 22c is made from a biodegradable and/or resorbable material. In some embodiments, at least one of extensions 22c is made from a biodegradable and/or resorbable material that degrades and/or resorbs at a faster rate than the pocket such that the pocket with the implantable medical device within the pocket remains after extensions 22c degrade and/or resorb. In some embodiments, at least one of extensions 23 is made from a single layer of material to allow extensions to degrade and/or resorb at a faster rate than the pocket, which is formed from two layers of material (e.g., first and second pieces 22a, 22b). In some embodiments, extensions 22c and first and second pieces 22a, 22b are made from the same material. In some embodiments, extensions 22c and first and second pieces 22a, 22b are made different materials. In some embodiments, at least one of extensions 22c is made from a first material and at least one of extensions 22c is made from a second material that is different than the first material. The first and second materials may include any of the materials discussed herein.

In some embodiments, at least one of extensions 22c is made from a hemostatic material. In some embodiments, at least one of extensions 22c has a hemostatic agent, such as, for example, one or more of the hemostatic agents discussed herein, applied to extensions 22c. The hemostatic agent may be applied to extensions 22c in the same manner the hemostatic agents discussed herein are applied to substrate 22. In some embodiments, extensions 22c each have the same amount of the hemostatic agent. In some embodiments, at least one of extensions 22c has a first amount of the hemostatic agent and at least one of extensions 22c has a second amount of the hemostatic agent that is different than the first amount. In some embodiments, at least one of extensions 22c includes a first hemostatic agent and at least one of extensions 22c includes a second hemostatic agent that is different than the first hemostatic agent. In some embodiments, at least one of extensions 22c includes an active pharmaceutical ingredient, such as, for example, one or more of the active pharmaceutical ingredients discussed herein, in addition to in in place of the hemostatic agent. In some embodiments, at least one of extensions 22c may be cut or otherwise severed from the pocket before or after anchorage device is implanted within a patient. In some embodiments, at least one of extensions 22c is scored to facilitate the removal of extensions 22c from the pocket. This allows a medical practitioner to customize anchorage device 20 such that anchorage device only includes the amount of extensions 22c required to secure anchorage device 20 within a patient. That is, any extraneous extensions 22c can be removed prior to or after implantation of anchorage device 20.

In some embodiments, first and second pieces 22a, 22b are portions of a single sheet that is bent to produce a fold at one end of the pocket or envelope. First and second pieces 22a, 22b are joined along sides of the pocket or envelope that extend transverse to the fold such that the fold and the sides of the pocket or envelope do not have any openings. First and second pieces 22a, 22b are not joined at an end of the pocket or envelope opposite the fold to define an opening at the end such that a medical device can be inserted through the opening and into a cavity defined by inner surfaces of first and second pieces 22a, 22b.

In some embodiments, first and second pieces 22a, 22b each include a mesh discussed herein. In some embodiments, first piece 22a includes a mesh including pores P having a first size and second piece 22b includes a mesh including pores P having a second size, wherein the first size is different than the first size. In some embodiments, the first size is greater than the second size. In some embodiments, the first size is less than the second size. In some embodiments, first and second pieces 22a, 22b each include a thin walled structure discussed herein. In some embodiments one of first and second pieces 22a, 22b includes a mesh discussed herein and the other one of first and second pieces 22a, 22b includes a thin walled structure discussed herein that does not have any pores or apertures.

In some embodiments, substrate 22 is a planar sheet, as shown in FIGS. 2, 3 and 6-8. In some embodiments, the planar sheet is in the form of a mesh. In some embodiments, the planar sheet is in the form of a thin walled structure. The planar sheet has a first side and an opposite second side, similar to a sheet of paper.

In some embodiments, the planar sheet can be manipulated about all or only a portion of an implantable medical device, such as, for example, one of the implantable medical devices discussed herein. In some embodiments, the planar sheet is moldable or bendable about the implantable medical device. That is, the planar sheet can be bent without breaking the planar sheet. In some embodiments, the planar sheet can be manipulated to form a tube, for example. In some embodiments, the planar sheet has a rigid configuration. That is, the planar sheet cannot be bent without breaking the planar sheet. In some embodiments, the planar sheet can be secured to tissue to support the implantable medical device at the treatment site. The planar sheet can be variously shaped, such as, for example, circular, oval, oblong, triangular, rectangular, square, polygonal, irregular, uniform, non-uniform, variable and/or tapered.

In some embodiments, fibers F, F1 are each made up a single thread, as shown in FIGS. 4-8. In some embodiments, fibers F extend perpendicular to fibers F1. Fibers F intersect fibers F1 along longitudinal axis L such that two adjacent fibers F and two adjacent fibers F1 form one of pores P therebetween. In some embodiments, fibers F are uniformly spaced apart from one another and fibers F1 are uniformly spaced apart from one another such that pores P all have the same size.

In some embodiments of the meshes shown in FIGS. 2-8, fibers F comprise a first material and fibers F1 comprise a second material. In some embodiments, the first material and the second material are the same material and include an agent, such as, for example, a hemostatic agent. The hemostatic agent can include one more hemostatic agent, such as, for example, epinephrine, tranexamic acid, chitosan and oxidized regenerated cellulose. In some embodiments, the hemostatic agent can include one or more of Spongostan®, Surgifoam®, Avitene, thrombin and Ostene® in addition to or in place of the hemostatic agents discussed above. In some embodiments, the hemostatic agent can include one or more of protamine, norepinephrine, desmopressin, lysine analogs, collagen, gelatin, polysaccharide spheres, mineral zeolite, bovine thrombin, pooled human thrombin, recombinant thrombin, gelatin and thrombin, collagen and thrombin, cyanacrylate, fibrin glue, polyethylene glycol, and glutaraldehyde in addition to or in place of the hemostatic agents discussed above. In some embodiments, the lysine analog is tranexamic acid and has the formula:

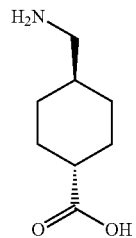

In some embodiments, the anchorage devices disclosed herein utilize one or more pharmacologic hemostatic agent since pharmacologic hemostatic agents have been found to be desirable over mechanical hemostats for a variety of reasons. Ethnographic research has showed that physicians desire a hemostat that can provide an extended elution profile to reduce bleeding events for up to 7 days' post operatively. Furthermore, there is a possible effect on handling and/or allergic reactions if mechanical hemostats, such as, for example, oxidized reduced cellulose or chitosan were used.

Figure 18:
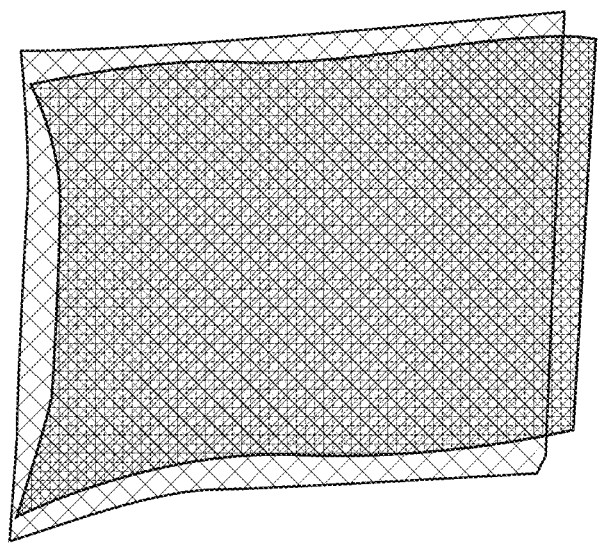
FIG. 18 is a perspective view of an anchorage device discussed in Example 9 in accordance with the principles of the present disclosure.

In some embodiments, tranexamic acid is preferred for use as hemostatic agent 24. Tranexamic acid is a synthetic analog of the amino acid lysine with a molecular weight of 157 g/mol. Tranexamic acid is an antifibrinolytic agent that acts by binding to plasminogen and blocking the interaction of plasminogen with fibrin, therefore preventing the dissolution of a fibrin clot. In the presence of a wound, fibrinolysis occurs naturally when a lysine residue such as tissue plasminogen activator (tPA), binds to plasmin causing the clot to lyse (or break). Tranexamic acid blocks tPA and keeps the clot from breaking, thus preventing unwanted bleeding. FIG. 18 depicts this process.

Prior to a damaged endothelium, tPA is inhibited in the blood by plasminogen activator inhibitor/type 1 (PAI-1). Once damage occurs, the tPA is released slowly into the blood, activating fibrinolysis. Excessive fibrinolysis results in a condition called hyperfibrinolysis, which requires intervention such as fibrinogen, plasma, transfusion or antifibrinolytic therapy, such as tranexamic acid.

Tranexamic acid has been used for over 40 years to reduce bleeding complications. Tranexamic acid is most commonly given systemically at doses of 10 mg/kg followed by infusion of 10 mg/kg/h. Since 2007, tranexamic acid has received widespread approval and clinical use as a hemostatic agent. Knowing that surgical trauma causes fibrinolysis in the area of the surgical wound itself, topical antifibrinolytic therapy is becoming more common to obtain and maintain hemostasis. Clinical trials with topical tranexamic acid use exist for cardiac surgery, CIED procedures, orthopedic surgery, spinal surgery, dental extraction and epistaxis, and breast mammoplasty.

To evaluate the efficacy of tranexamic acid, a non-GLP acute porcine study was conducted. Doses of 1 mg to 200 mg of tranexamic acid were used in an in vitro whole blood coagulation test, a hepatic biopsy test, and a subcutaneous ICD surgical procedure.

The in vitro whole blood coagulation test showed no activity for tranexamic acid up to 10 mg/ml. The maximum tranexamic acid concentration, 200 mg/5 ml, was a slightly higher dose than that used clinically in a CIED pocket if 50 cc is the assumed blood volume of interest. Coagulation time was doubled with this higher dose.

The hepatic biopsy test had a volume of 0.016 ml when the biopsy hole was filled with blood. The minimum tranexamic acid dose evaluated was 2.5 mg, which is equivalent to 156 mg/ml. This concentration prevents blood from clotting quickly and these biopsies continued to bleed past the endpoint of 10 minutes. This phenomenon is likely due to the multiple bonding sites available to tranexamic acid in whole blood, and the fact that a biopsy does not induce fibrinolysis.

The subcutaneous surgical site test was conducted with an elevated ACT using heparin to induce hematoma. Surgical trauma similar to that of a CIEO implant was incurred in each pocket, but some subcutaneous pockets incurred more trauma than others due to anatomical location. The primary output monitored was accumulated blood as measured by pre-weighed gauze 3-hours post-operatively. With only one animal, and two pockets per treatment, the sample size was too low to show any significance between ICD only, ICD+ polymer, and ICD+polymer+tranexamic acid.

The non-GLP acute porcine study showed that in the dose range evaluated, tranexamic acid has a two-fold increase on clotting time and no effect on reducing bleeding on the hepatic biopsies. In the heparinized ICD pocket procedure, 3.5-22.8 grams of blood accumulated in a 3-hour period of time regardless of treatment. It appears that subcutaneous pockets in an anticoagulated porcine model would be a translatable model for evaluating efficacy of tranexamic acid because it has a relevant volume of accumulated blood and surgical trauma similar to that of a CIED procedure.

Based upon the non-GLP acute porcine study, tranexamic acid concentrations of 3.00 mg/L to 30 mg/L are effective in preventing fibrinolysis. As such, in some embodiments, hemostatic agent 24 is tranexamic acid and is provided in concentrations of about 3.00 mg/L to about 30 mg/L. However, it has been found that one tenth of the doses used in the non-GLP acute porcine study can be effective in reversing fibrinolysis. As such, in some embodiments, hemostatic agent 24 is tranexamic acid and is provided in concentrations of about 0.30 mg/L to about 3.0 mg/L for intravenous applications. In some embodiments, tranexamic acid is provided in concentrations of about 3.78 mg/L to about 30 mg/L for topical applications as well. However, in some embodiments, however, higher doses of tranexamic acid are used for topical applications to account for tranexamic acid being widely distributed throughout the extracellular and intracellular compartments when given preoperatively. Indeed, it has been found that tranexamic acid reaches plasma concentrations in 5-15 minutes. As such, in some embodiments, tranexamic acid is provided in doses of about 1.5 mg to about 150 mg.

Figure 2:
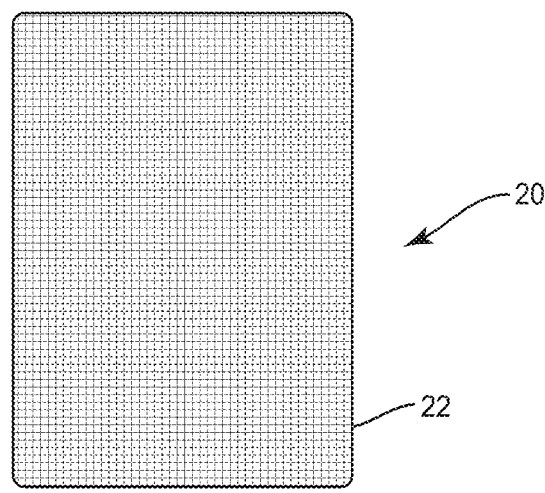
FIG. 2 is a perspective view of one embodiment of the anchorage device shown in FIG. 1 in accordance with the principles of the present disclosure.
Figure 3:
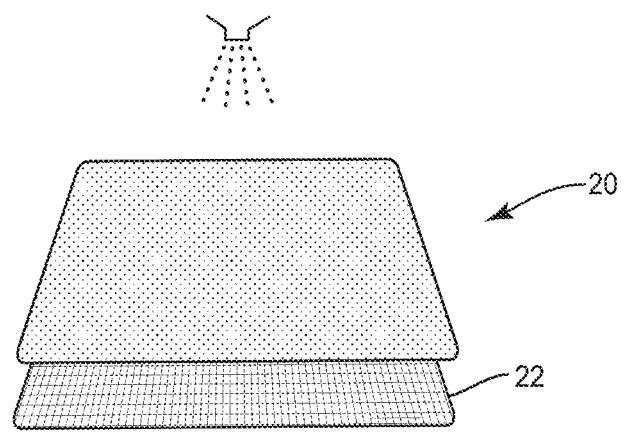
FIG. 3 is a perspective view of one embodiment of the anchorage device shown in FIG. 1 in accordance with the principles of the present disclosure.

In some embodiments, fibers F and fibers F1 are made from the hemostatic agent. In some embodiments, fibers F and fibers F1 are sprayed with the hemostatic agent. In some embodiments, fibers F and fibers F1 are coated with the hemostatic agent. In some embodiments, fibers F and fibers F1 are washed with the hemostatic agent. In some embodiments, the hemostatic agent is printed onto fibers F and fibers F1 using a 3D printer for example. In one embodiment, the mesh is made from the hemostatic agent, as shown in FIG. 2. That is, at least one of fibers F and fibers F1 are made from the hemostatic agent. In one embodiment, the mesh is made from the hemostatic agent and the hemostatic mesh is coated with an active pharmaceutical agent, such as, for example, an antibiotic, as shown in FIG. 3.

In some embodiments of the meshes discussed herein, the first material and the second material are different materials and only one of the first and second materials includes the hemostatic agent. For example, in one embodiment, the first material comprises the hemostatic agent and the second material does not. In another embodiment, the second material comprises the hemostatic agent and the first material does not. In some embodiments, fibers F or fibers F1 are made from the hemostatic agent (e.g., one of the first and second materials). In some embodiments, fibers F or fibers F1 are sprayed with the hemostatic agent (e.g., one of the first and second materials). In some embodiments, fibers F or fibers F1 are coated with the hemostatic agent (e.g., one of the first and second materials). In some embodiments, fibers F or fibers F1 are washed with the hemostatic agent (e.g., one of the first and second materials). In some embodiments, the hemostatic agent (e.g., one of the first and second materials) is printed onto fibers F or fibers F1 using a 3D printer for example.

In some embodiments of the meshes discussed herein, the first material and the second material are different materials, wherein only one of the first and second materials includes the hemostatic agent and the other one of the first and second materials includes an active pharmaceutical ingredient, such as, for example, active pharmaceutical ingredient. The active pharmaceutical ingredient can include one or a combination of active pharmaceutical ingredients, such as, for example, anesthetics, antibiotics, anti-inflammatory agents, procoagulant agents, fibrosis-inhibiting agents, anti-scarring agents, antiseptics, leukotriene inhibitors/antagonists, cell growth inhibitors and mixtures thereof. In some embodiments, the active pharmaceutical ingredient is an antibiotic. In some embodiments, the antibiotic is selected from the group consisting of rifampin and minocycline and mixtures thereof.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antibacterial agents or antimicrobials include, but are not limited to, triclosan, chlorohexidine and other cationic biguanides, rifampin, minocycline (or other tetracycline derivatives), vancomycin, gentamycin; gendine; genlenol; genfoctol; clofoctol; cephalosporins and the like. Further antibacterial agents or antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; hexachlorophene; cefamandole nafate; cefepime and its hydrochloride, sulfate, and phosphate salt; cefdinir and its sodium salt; ceftriaxone and its sodium salt; cefixime and its sodium salt; cetylpyridinium chloride; ofoxacin; linexolid; temafloxacin; fleroxacin; enoxacin; gemifloxacin; lomefloxacin; astreonam; tosufloxacin; clinafloxacin; cefpodoxime proxetil; chloroxylenol; methylene chloride, iodine and iodophores (povidone-iodine); nitrofurazone; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; α-terpineol; thymol; taurinamides; nitrofurantoin; silver-sulfadiazine; hexetidine; methenamine; aldehydes; azylic acid; silver; benzyl peroxide; alcohols; carboxylic acids; salts; nafcillin; ticarcillin and its disodium salt; sulbactam and its sodium salt; methylisothiazolone, moxifloxacin; amifloxacin; pefloxacin; nystatin; carbepenems; lipoic acids and its derivatives; beta-lactams antibiotics; monobactams; aminoglycosides; microlides; lincosamides; glycopeptides; tetracyclines; chloramphenicol; quinolones; fucidines; sulfonamides; macrolides; ciprofloxacin; ofloxacin; levofloxacins; teicoplanin; mupirocin; norfloxacin; sparfloxacin; ketolides; polyenes; azoles; penicillins; echinocandines; nalidixic acid; rifamycins; oxalines; streptogramins; lipopeptides; gatifloxacin; trovafloxacin mesylate; alatrofloxacin mesylate; trimethoprims; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin (and combinations thereof). In some embodiments, the polymer may contain rifampin and another antimicrobial agent, such as, for example, an antimicrobial agent that is a tetracycline derivative. In some embodiments, the polymer contains a cephalosporin and another antimicrobial agent. In some embodiments, the polymer contains combinations including rifampin and minocycline, rifampin and gentamycin, and rifampin and minocycline.

When a mixture of two antibiotics is used, they generally present in a ratio ranging from about 10:1 to about 1:10. In some embodiments, a mixture of rifampin and minocycline are used. In those embodiments, a ratio of rifampin to minocycline ranges from about 5:2 to about 2:5. In other embodiments, the ratio of rifampin to minocycline is about 1:1.

Examples of antifungals include amphotericin B; pyrimethamine; flucytosine; caspofungin acetate; fluconazole; griseofulvin;terbinafine and its hydrochloride, sulfate, or phosphate salt; amorolfine; triazoles (Voriconazole); flutrimazole; cilofungin; LY303366 (echinocandines); pneumocandin; imidazoles; omoconazole; terconazole; fluconazole; amphotericin B, nystatin, natamycin, liposomal amptericin B, liposomal nystatins; griseofulvin; BF-796; MTCH 24; BTG-137586; RMP-7/Amphotericin B; pradimicins; benanomicin; ambisome; ABLC; ABCD; Nikkomycin Z; flucytosine; SCH 56592; ER30346; UK 9746; UK 9751; T 8581; LY121019; ketoconazole; micronazole; clotrimazole; econazole; ciclopirox; naftifine; and itraconazole.

In some embodiments, active pharmaceutical ingredient 26 includes keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

In some embodiments, active pharmaceutical ingredient 26 includes one or more ingredients that act as angiogenensis inhibitors or inhibit cell growth such as epidermal growth factor, PDGF, VEGF, FGF (fibroblast growth factor) and the like. These ingredients include anti-growth factor antibodies (neutrophilin-1), growth factor receptor-specific inhibitors such as endostatin and thalidomide. Examples of useful proteins include cell growth inhibitors such as epidermal growth factor.

Examples of anti-inflammatory compounds include, but are not limited to, anecortive acetate; tetrahydrocortisol, 4,9(11)-pregnadien-17α, 21-diol-3,20-dione and its -21-acetate salt; 111-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

In some embodiments, active pharmaceutical ingredient 26 includes sodium 2-mercaptoethane sulfonate ("MESNA"). MESNA has been shown to diminish myofibroblast formation in animal studies of capsular contracture with breast implants [Ajmal et al. (2003) Plast. Reconstr. Surg. 112:1455-1461] and may thus act as an anti-fibrosis agent.

Procoagulants include, but are not limited to, zeolites, thrombin, and coagulation factor concentrates.

In one embodiment, the first material comprises the hemostatic agent and the second material comprises the active pharmaceutical ingredient. In another embodiment, the second material comprises the hemostatic agent and the first material comprises the active pharmaceutical ingredient. In some embodiments, fibers F or fibers F1 are made from the hemostatic agent (e.g., one of the first and second materials) and/or the active pharmaceutical ingredient (e.g., one of the first and second materials). In some embodiments, fibers F or fibers F1 are sprayed with the hemostatic agent (e.g., one of the first and second materials) or the active pharmaceutical ingredient (e.g., one of the first and second materials). In some embodiments, fibers F or fibers F1 are coated with the hemostatic agent (e.g., one of the first and second materials) or the active pharmaceutical ingredient (e.g., one of the first and second materials). In some embodiments, fibers F or fibers F1 are washed with the hemostatic agent (e.g., one of the first and second materials) or the active pharmaceutical ingredient (e.g., one of the first and second materials). In some embodiments, the hemostatic agent (e.g., one of the first and second materials) or the active pharmaceutical ingredient (e.g., one of the first and second materials) is printed onto fibers F or fibers F1 using a 3D printer for example.

In some embodiments of the meshes discussed herein, the first material includes only the hemostatic agent the second material includes the hemostatic agent and the active pharmaceutical ingredient. In some embodiments, the second material has the active pharmaceutical ingredient in an outer layer such that the active pharmaceutical ingredient is in an outer layer of the fibers that are made from the second material. As such, when substrate 22 is implanted within a patient, one of fibers F and fibers F1 will elute the hemostatic agent upon implantation and the other one of fibers F and fibers F1 will elute the active pharmaceutical ingredient upon implantation. After the active pharmaceutical ingredient has eluted from the fibers that include the second material, the hemostatic agent will elute from the second material. As such, anchorage device 20 can elute both the hemostatic agent and the active pharmaceutical agent upon implantation and then elute only the hemostatic agent after implantation. In some embodiments, the second material has the active pharmaceutical agent in an inner layer such that the active pharmaceutical agent is in an inner layer of the fibers that are made from the second material. As such, when substrate 22 is implanted within a patient, fibers F and fibers F1 will both elute the hemostatic agent upon implantation. After the hemostatic agent has eluted from the fibers that include the second material, the active pharmaceutical ingredient will elute from the second material. As such, anchorage device 20 can elute only the hemostatic agent upon implantation and then elute the hemostatic agent and the active pharmaceutical ingredient after implantation.

In some embodiments of the meshes discussed herein, the first material includes only the active pharmaceutical ingredient the second material includes the hemostatic agent and the active pharmaceutical ingredient. In some embodiments, the second material has the active pharmaceutical ingredient in an outer layer such that the active pharmaceutical ingredient is in an outer layer of the fibers that are made from the second material. As such, when substrate 22 is implanted within a patient, both fibers F and fibers F1 will elute the active pharmaceutical ingredient upon implantation. After the active pharmaceutical ingredient has eluted from the fibers that include the second material, the hemostatic agent will elute from the second material. As such, anchorage device 20 can elute only the active pharmaceutical agent upon implantation and then elute the hemostatic agent and the active pharmaceutical ingredient after implantation. In some embodiments, the second material has the active pharmaceutical agent in an inner layer such that the active pharmaceutical agent is in an inner layer of the fibers that are made from the second material. As such, when substrate 22 is implanted within a patient, one of fibers F and fibers F1 will elute the hemostatic agent upon implantation and one of fibers F and fibers F1 will elute the hemostatic agent upon implantation. After the hemostatic agent has eluted from the fibers that include the second material, the active pharmaceutical ingredient will elute from the second material. As such, anchorage device 20 can elute both the hemostatic agent and the active pharmaceutical ingredient upon implantation and then elute only the active pharmaceutical ingredient after implantation.

In some embodiments, the first material and/or the second material may include one or a plurality of discrete layers. As such, fibers F and/or fibers F1 may include a plurality of discrete layers, such as, for example, a first layer, a second layer, a third layer, a fourth layer, a fifth layer, etc. In some embodiments, at least one of the layers is different than another one of the other layers. It is envisioned that the first material and/or the second material each may include any number of layers. In some embodiments, the first material and/or the second material each include the same number of layers such that fibers F and fibers F1 each include the same number of layers. For example, fibers F and fibers F1 may each include 1 layer, 2 layers, 3 layers, 4 layers, 5 layers, etc. In some embodiments, the first material and/or the second material may include different numbers of layers such that fibers F and fibers F1 also have a different number of layers. For example, fibers F may include one layer while fibers F1 include two layers, and vice versa; fibers F may include two layers while fibers F1 include three layers, and vice versa; fibers F may include three layers while fibers F1 include four layers, and vice versa; fibers F may include four layers while fibers F1 include five layers, etc. In some embodiments, one of fibers F and fibers F1 include a single layer and the other one of fibers F and F1 include a plurality of layers.

In some embodiments, the layers each include the hemostatic agent and/or the active pharmaceutical ingredient. In some embodiments, the contents of the layers' alternate. For example, in some embodiments, the first layer of each fiber F includes the active pharmaceutical ingredient, the second layer of each fiber F1 includes the hemostatic agent, the third layer of each fiber F1 includes the active pharmaceutical ingredient, the fourth layer of each fiber F1 includes the hemostatic agent and the fifth layer of each fiber F1 includes the active pharmaceutical ingredient, wherein the layers that include the hemostatic agent do not include the active pharmaceutical ingredient and the layers that include the active pharmaceutical ingredient do not include the hemostatic agent. Likewise, in some embodiments, the first layer of each fiber F1 includes the hemostatic agent, the second layer of each fiber F1 includes the active pharmaceutical agent, the third layer of each fiber F1 includes the hemostatic agent, the fourth layer of each fiber F1 includes the active pharmaceutical agent and the fifth layer of each fiber F1 includes the hemostatic agent, wherein the layers that include the hemostatic agent do not include the active pharmaceutical ingredient and the layers that include the active pharmaceutical ingredient do not include the hemostatic agent. In some embodiments, the first layers are inner layers and the fifth layers are outer layers. In some embodiments, the first layers are outer layers and the fifth layers are inner layers. In some embodiments, the layers each include the hemostatic agent and/or the active pharmaceutical ingredient, wherein the amount of the hemostatic agent and/or the active pharmaceutical ingredient in each layer is the same or different.

In some embodiments, the layers that form the first material and/or the second material may be made of at least one polymer. This allows the hemostatic agents and/or the active pharmaceutical ingredients to be applied to fiber F and/or fiber F1 via a polymer that coats at least a portion of each of fibers F and/or fibers F1. In some embodiments, the polymer includes a combination, blend or mixture of polymers. In some embodiments, the polymer is configured to degrade within a patient and releases the hemostatic agent and/or the active pharmaceutical ingredient as the polymer degrades. In some embodiments, the degradation rate of the polymer is known or can be predicted to allow a medical practitioner to select a polymer or a quantity of polymer that is applied to fibers F and/or fibers F1 to produce anchorage device 20 that is customized to elute a selected quantity of the hemostatic agent and/or the active pharmaceutical ingredient at a selected rate over a selected period of time. For example, the polymer may be selected to elute a selected quantity of the hemostatic and/or the active pharmaceutical ingredient per hour or day for a selected number of days or hours.

In some embodiments, the polymer is selected from the group consisting of polylactic acid, polyglycolic acid, poly (L-lactide), poly(D,L-lactide)polyglycolic acid[polyglycolide], poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polyethylene oxide, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly(phosphazene), poly(phosphate ester), poly(amino acid), polydepsipeptides, maleic anhydride copolymers, polyiminocarbonates, poly [(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose. In some embodiments, the polymer may include combinations, blends or mixtures of the polymers discussed herein.

In some embodiments, the polymer is a polyarylate. In some embodiments, the polymer is a tyrosine-derived polyarylate. In some embodiments, the tyrosine-derived polyarylate is p(DTE co X % DT succinate), where X is about 10% to about 30%. In some embodiments, the tyrosine-derived polyarylate is p(DTE co X % DT succinate), where X ranges from about 26.5% to about 28.5%. In some embodiments, the tyrosine-derived polyarylate is p(DTE co X % DT succinate), where X is about 27.5%. In some embodiments, the polymer is P22-27.5 DT.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22-XX is a polyarylate copolymer produced by condensation of DTE and DTBn with succinic acid followed by removal of benzyl group. P22-10, P22-15, P22-20, P22-XX, etc., represents copolymers different percentage of DT (i.e., 10, 15, 20 and % DT, etc.) In some embodiments, the polymer is produced by condensation of DTBn with succinic acid followed by removal of benzyl group. This polymer is represented as P02-100.

In some embodiments, the polymer includes one or more polyarylates that are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. In some embodiments, the DT or BT contents include those copolymers with from about 1% to about 30%, from about 5% to about 30% from about 10 to about 30% DT or BT. In some embodiments, the diacids (used informing the polyarylates) include succinate, glutarate and glycolic acid.

In some embodiments, the polymer includes one or more biodegradable, resorbable polyarylates and polycarbonates. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate, DT PEG ester succinate, DTMB P(Desaminotyrsoyl tyrosine methylparaben ester-glutarate), and DTPP P(Desaminotyrsoyl tyrosine propylparaben ester-glutarate).

In some embodiments, the polymer is one more polymers from the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT. In some embodiments, the polymer is P22-27.5 DT.

In some embodiments, the polymer has diphenol monomer units that are copolymerized with an appropriate chemical moiety to form a polyarylate, a polycarbonate, a polyiminocarbonate, a polyphosphonate or any other polymer.

In some embodiments, the polymer is tyrosine-based polyarylate. In some embodiments, the polymer includes blends and copolymers with polyalkylene oxides, including polyethylene glycol (PEG).

In some embodiments, the polymer can have from 0.1-99.9% PEG diacid to promote the degradation process. In some embodiments, the polymer includes blends of polyarylates or other biodegradable polymers with polyarylates.

The polymer is configured to release the hemostatic and/or the active pharmaceutical ingredient over time, as discussed herein. In some embodiments, the polymer is configured to release the hemostatic and/or the active pharmaceutical ingredient over a time period ranging from about 1 hour to about 168 hours. In some embodiments, the polymer is configured to release the hemostatic and/or the active pharmaceutical ingredient over a time period ranging from 1 hour to 72 hours. In some embodiments, the polymer is configured to release the hemostatic and/or the active pharmaceutical ingredient over a time period ranging from 1 hour to 24 hours.

In some embodiments, the polymer is configured to release the hemostatic and/or the active pharmaceutical ingredient over time in an area surrounding or adjacent to anchorage device 20 (such as, for example, within the device "pocket" or within 3 inches in all dimensions). In some embodiments, the polymer is configured to release the hemostatic and/or the active pharmaceutical ingredient for up to 30 hours. In some embodiments, the polymer is configured to release between about 40% and about 100% of the hemostatic and/or the active pharmaceutical ingredient over a period of at least about 30 hours. In some embodiments, the polymer is configured to release 60% and about 100% of the hemostatic and/or the active pharmaceutical ingredient over a period of at least about 30 hours. In some embodiments, the polymer is configured to release between about 65% and about 100% of the hemostatic and/or the active pharmaceutical ingredient over a period of at least about 36 hours. In some embodiments, the polymer is configured to release 80% and about 100% of the hemostatic and/or the active pharmaceutical ingredient over a period of at least about 36 hours. In some embodiments, the polymer is configured to release between about 60% and about 100% of the hemostatic and/or the active pharmaceutical ingredient over a period of at least about 48 hours. In some embodiments, the polymer is configured to release 80% and about 100% of the hemostatic and/or the active pharmaceutical ingredient over a period of at least about 48 hours. In some embodiments, the polymer is configured to release between about 60% and about 100% of the hemostatic and/or the active pharmaceutical ingredient over a period of at least about 60 hours. In some embodiments, the polymer is configured to release 80% and about 100% of the hemostatic and/or the active pharmaceutical ingredient over a period of at least about 60 hours. In some embodiments, the polymer is configured to release 80% and about 100% of the hemostatic and/or the active pharmaceutical ingredient within 48 hours. In some embodiments, the polymer is configured to release 80% and about 100% of the hemostatic and/or the active pharmaceutical ingredient within 24 hours.

In some embodiments, the polymer is configured to release no more than 60% of the hemostatic and/or the active pharmaceutical ingredient 24 within 24 hours. In some embodiments, the polymer is configured to release no more than 90% of the hemostatic and/or the active pharmaceutical ingredient after 60 hours. In some embodiments, the polymer is configured to release no more than 50% of the hemostatic and/or the active pharmaceutical ingredient within 12 hours. In some embodiments, the polymer is configured to release of the hemostatic and/or the active pharmaceutical ingredient between about 40% and about 90% between 12 and 24 hours. In some embodiments, the polymer is configured to release between about 60% and about 100% of the hemostatic and/or the active pharmaceutical ingredient between 24 and 36 hours. In some embodiments, the polymer is configured to release between about 65% and about 100% of the hemostatic and/or the active pharmaceutical ingredient between 36 and 48 hours. In some embodiments, the polymer is configured to release between about 70% and about 100% of the hemostatic and/or the active pharmaceutical ingredient between 48 and 60 hours.

As discussed herein, the first material and/or the second material may include one or a plurality of polymer coatings. That is, fibers F and/or fibers F1 may be coated with single or multiple coating layers of the polymer, depending on, for example, the amount of the hemostatic and/or the active pharmaceutical ingredient to be delivered and desired release rate. Each layer of the polymer may contain the same or different amounts of the hemostatic and/or the active pharmaceutical ingredient. For example, a first layer of the polymer may contain the hemostatic and/or the active pharmaceutical ingredient, while the second layer of the polymer contains either none of the hemostatic and/or the active pharmaceutical ingredient or a lower concentration of the hemostatic and/or the active pharmaceutical ingredient. As another example, a first layer of the polymer may comprise the hemostatic and/or the active pharmaceutical ingredient in a first polymer, while the second layer of the polymer comprises the hemostatic and/or the active pharmaceutical ingredient in a second polymer that is different than the first polymer.

In some embodiments of the meshes discussed herein, every other one of fibers F and/or fibers F1 are made from a first material and every other one of fibers F and/or fibers F1 are made from a second material. For example, fibers Fa and Fc may include one of the first and second materials and fiber Fb may include the other one of the first and second materials (see FIGS. 7 and 9). Likewise, fibers F1a and F1c may include one of the first and second materials and fiber F1b may include the other one of the first and second materials (see FIGS. 7 and 9). The first and second materials have been discussed above.

Figure 10:
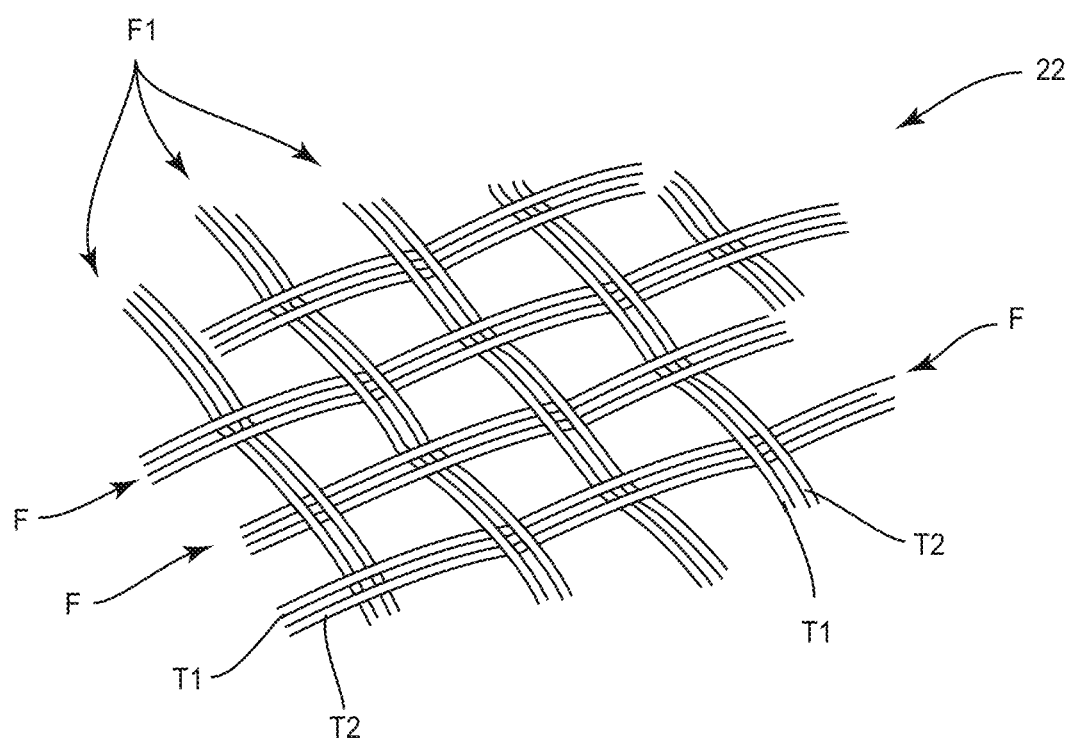
FIG. 10 is a perspective, close-up view of a portion of one embodiment of the anchorage device shown in FIG. 1 in accordance with the principles of the present disclosure.
Figure 11:
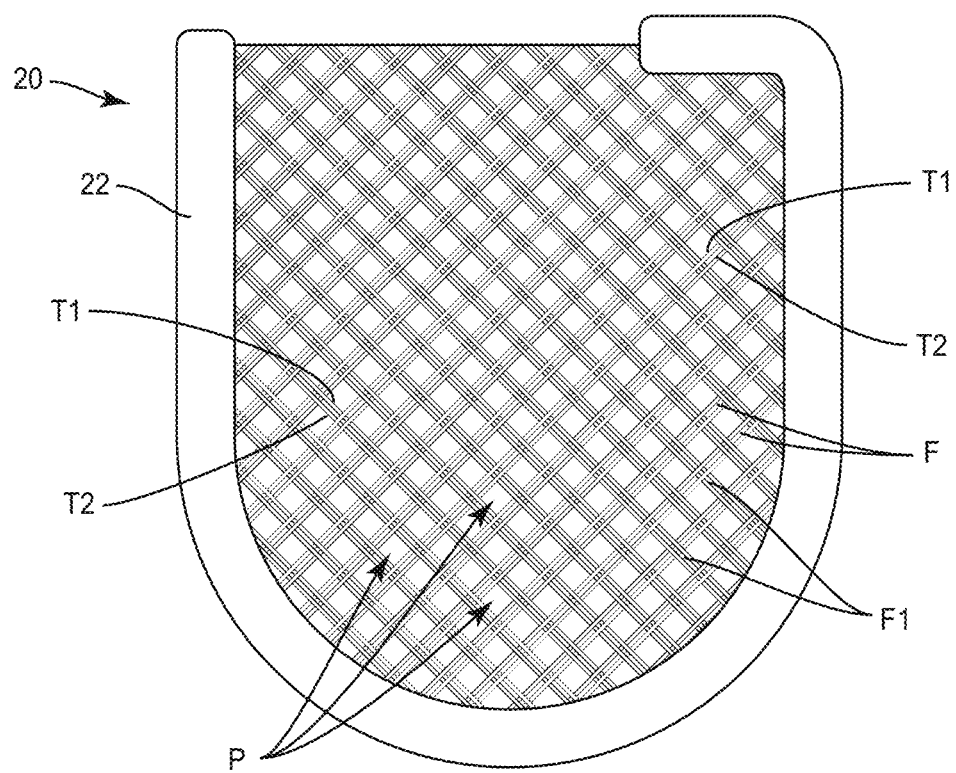
FIG. 11 is a top view of one embodiment of the anchorage device shown in FIG. 1 in accordance with the principles of the present disclosure.

In some embodiments, fibers F and/or F1 are each made up a plurality of threads, such as, for example, thread T1 and thread T2, as shown in FIGS. 10 and 11. That is, threads T1, T2 combine to form fibers F and/or fibers F1. In some embodiments, one of fibers F and fibers F1 are made up of multiple threads, such as, for example, threads T1 and T2, and the other one of fibers F and fibers F1 are made up of a single thread. In some embodiments, threads T1 of fibers F and/or fibers F1 are made from the first material and threads T2 of fibers F and/or fibers F1 are made from the second material. In some embodiments, threads T1, T2, of fibers F are made from the first material and threads T1, T2 of fibers F1 are made from the second material. The first and second materials have been discussed above.

Figure 12:
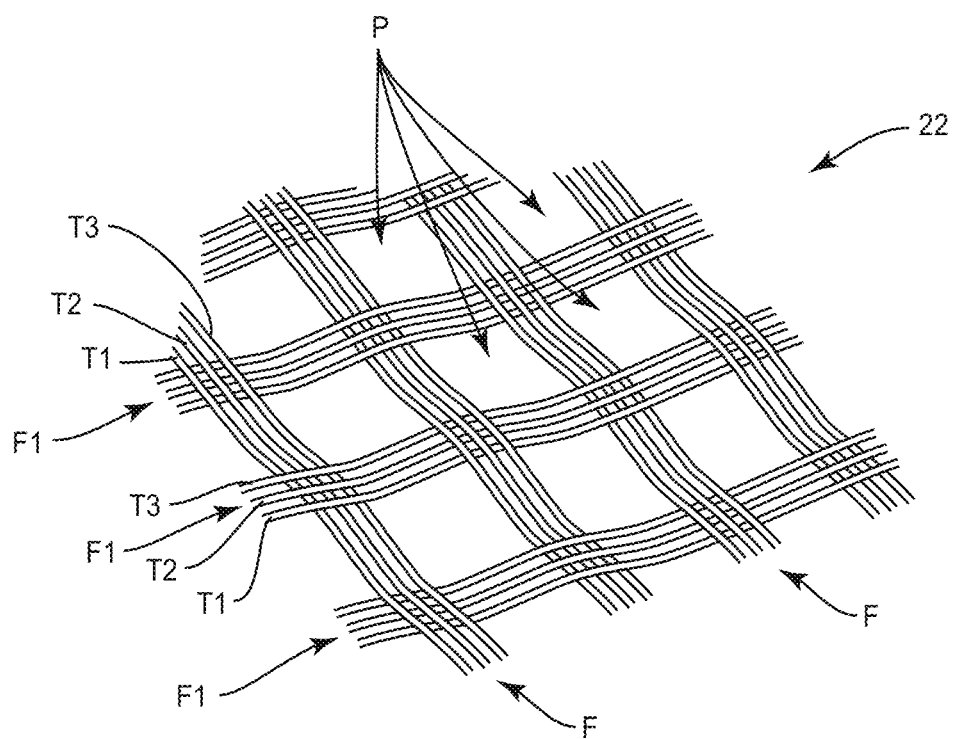
FIG. 12 is a top view of one embodiment of the anchorage device shown in FIG. 1 in accordance with the principles of the present disclosure.

In some embodiments, fibers F and/or fibers F1 are each made up a plurality of threads, such as, for example, thread T1, thread T2 and thread T3, as shown in FIG. 12. That is, threads T1, T2, T3 combine to form fibers F and fibers F1. In some embodiments, one of fibers F and fibers F1 are made up of multiple threads, such as, for example, threads T1, T2 and T3, and the other one of fibers F and fibers F1 are made up of a single thread. In some embodiments, threads T1, T3 of fibers F and/or fibers F1 are made from the first material and threads T2 of fibers F and/or fibers F1 are made from the second material. In some embodiments, threads T1, T3 of fibers F and/or fibers F1 are made from the second material and threads T2 of fibers F and/or fibers F1 are made from the first material. In some embodiments, threads T1, T2, T3 of fibers F are made from the first material and threads T1, T2, T3 of fibers F1 are made from the second material. The first and second materials have been discussed above.

Figure 13:
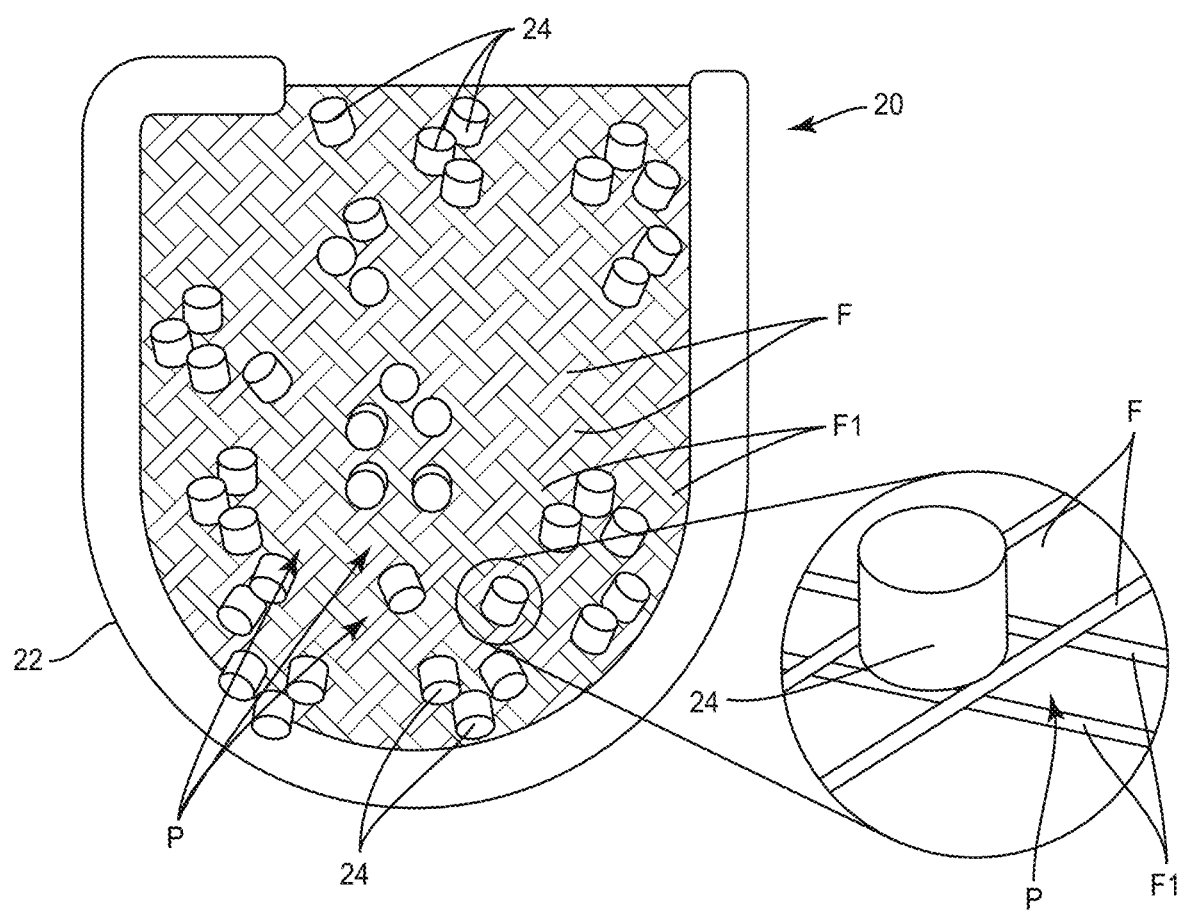
FIG. 13 is a top view of one embodiment of the anchorage device shown in FIG. 1 in accordance with the principles of the present disclosure.

In one embodiment, shown in FIG. 13, substrate 20 includes one or a plurality of plugs 24 that are positioned within pores P defined by fibers F and fibers F1. In some embodiments, plugs 24 comprise one or more polymers, such as, for example, one or more of the polymers discussed herein. In some embodiments, the polymer(s) that make up plugs 24 include an agent, such as, for example, at least one of the hemostatic agents discussed herein and/or at least one of the active pharmaceutical ingredients discussed herein.

As such, plugs 24 provide a means to provide agents to a treatment area in addition to the agents provided by fibers F and/or fibers F1. In some embodiments, fibers F and/or fibers F1 do not include any agents, such as, for example, at least one of the hemostatic agents discussed herein and/or at least one of the active pharmaceutical ingredients discussed herein, and the agents are included only in plugs 24. This allows plugs 24l to be selectively positioned in pores 24 such that the positioning of plugs 24 corresponds to a targeted area, such as, for example, an area that may have at least some risk of bleeding and/or at least some risk of infection. That is, once an area that is thought to include some risk of bleeding and/or at least some risk of infection is identified, plugs 24 can be selectively positioned in substrate 22 such that plugs 24 will be positioned adjacent to the identified area once anchorage device is implanted within a patient to prevent, reduce or eliminate the bleeding and/or infection.

It is contemplated that the thin walled structures discussed herein may also be made up of fibers, such as, for example fibers F and/or fibers F1. However, in embodiments wherein substrate 22 comprises the thin walled structure, the fibers are arranged such that the pores of the thin walled structure are smaller than pores P or such that the thin walled structure does not include any pores defined by the fibers. That is, the fibers may be arranged tightly together such that there is no space between adjacent fibers.

In some embodiments, anchorage device 20 includes a hydrophilic component, such as, for example, PEG and a crosslinking agent that is applied to substrate 22. The hydrophilic component and the crosslinking agent form a hydrogel that absorbs blood and reduces bleeding when in contact with blood or tissue fluid. In some embodiments, the hydrophilic component and the crosslinking agent are sprayed directly onto substrate 22. In some embodiments, the hydrophilic component and the crosslinking agent are provided in a polymer, such as, for example, one or more of the polymers discussed herein, and the polymer is applied directly onto substrate 22. In some embodiments, the hydrophilic component and the crosslinking agent are provided in a patch, such as, for example, the Veriset™ hemostatic patch available from Medtronic, Inc., and the patch is applied directly onto substrate 22. In some embodiments, the patch comprises a plurality of layers. For example, a first layer of the patch can include a hemostatic agent, such as, for example, oxidized regenerated cellulose and/or one or more of the hemostatic agents discussed herein. A second layer of the patch can include a crosslinking agent, such as, for example, trilysine and/or one or more of the crosslinking agents discussed herein. A third layer of the patch can include a hydrophilic agent, such as, for example, PEG and/or one or more of the hydrophilic agents discussed herein. The second layer of the patch is positioned between the first and third layers of the patch.

In some embodiments, the hydrophilic component comprises thermogelling hydrogels, PEG-PLGA copolymers, PEG-Poly(N-isopropyl acrylamide), Pluronic (PEO-PPO-PEO triblock), PEG-PCL polymers, PEG-based amphiphilic copolymers modified by anionic weak polyelectrolytes, (such as polyacrylic acid, polyglutamic acid) and polymers containing sulfonamide groups), PEG-based amphiphilic copolymers modified by cationic weak polyelectrolytes (such as poly (2-vinyl pyridine), Poly(beta-amino esters), poly (2-(dimethylamino)ethyl methacrylate), multiarm PEG derivatives such as those available from JenKem technology, multiarmed block and graft PLA copolymers with PEG, PEG with stereo complexed poly(lactide), acrylated polymers (such as Polyvinylalcohol, dextran, Polyvinylpyrollidone, chitosan, alginate, hyaluronic acid), and combinations thereof. In some embodiments, the crosslinking agent comprises one or more agents that induce polymerization of vinyl groups using various initiators, light or redox reactions, or by reactions such as Schiff base formation, Michael type additions, peptide ligation, clock chemistry of functional groups present; one or more agents that induce crosslinking by enzymatic reaction (transglutaminase mediated reaction between carboxamide and amine on proteins), stereo-complexation, metal chelation (alginates using calciumCal2), thermogelation, self-assembly (formation of super helices from protein chains) inclusion complexation (using cyclodextrin); and combinations thereof.

Methods

In some embodiments, an anchorage device, such as, for example, anchorage device 20 and a medical device, such as, for example, one of the implantable medical devices discussed herein are implanted into a body of a patient. The anchorage device releases a hemostatic agent, such as, for example, at least one of the hemostatic agents discussed herein to reduce or prevent bleeding within the patient. In some embodiments, the anchorage device also releases an active pharmaceutical agent, such as, for example, at least one of the active pharmaceutical ingredients discussed herein to prevent, mitigate, or treat a condition within the patient, such as, for example, a bacterial infection. In some embodiments, the anchorage device releases the hemostatic agent before the active pharmaceutical ingredient. In some embodiments, the anchorage device releases the hemostatic agent after the active pharmaceutical ingredient. In some embodiments, the anchorage device releases the hemostatic agent and the active pharmaceutical ingredient simultaneously. In some embodiments, the anchorage device releases the hemostatic agent and/or the active pharmaceutical ingredient upon implantation of the anchorage device. In some embodiments, the anchorage device releases the hemostatic agent and the active pharmaceutical ingredient in alternating sequences. In some embodiments, the anchorage device is implanted within the patient without the medical device and the medical device is coupled to or inserted into the anchorage device after the anchorage device is implanted. In some embodiments, the medical device is coupled to or inserted into the anchorage device before the anchorage device is implanted within the patient and the anchorage device and the medical device are implanted within the patient together.

In some embodiments, the implantable medical device is removed from the patient after the treatment is completed. In some embodiments, the anchorage device remains implanted within the patient after the implantable medical device is removed. In some embodiments, the anchorage device is removed from the patient after the implantable medical device is removed. To remove the anchorage device, tissue that is ingrown within the substrate of the anchorage device can be cut or otherwise detached from the substrate. In some embodiments, a portion of the anchorage device may not be removable from the tissue and will remain implanted within the patient.

Kits

In some embodiments, kits are provided that include one or a plurality of anchorage devices, such as, for example, anchorage devices 20. It is contemplated that each of the anchorage devices included can have a different configuration. In some embodiments, the anchorage devices can include different hemostatic agents, such as, for example, at least one of the hemostatic agents discussed herein and/or different active pharmaceutical ingredients, such as, for example, at least one of the active pharmaceutical ingredients discussed herein. In some embodiments, the anchorage devices can include different amounts of a hemostatic agent, such as, for example, the hemostatic agents discussed herein and/or different amounts of an active pharmaceutical ingredient, such as, for example, the active pharmaceutical ingredients discussed herein. In some embodiments, the anchorage devices can include different sizes. In some embodiments, the anchorage devices can include different shapes. In some embodiments, the anchorage devices can include different anchorage devices that are designed for use with different medical devices, such as, for example, the implantable or non-implantable medical devices discussed herein. In some embodiments, the kits include one or a plurality of medical devices, such as, for example, the implantable or non-implantable medical devices discussed herein. In some embodiments, the kit includes instructions for use.

Example 1

In one example, an anchorage device having a substrate, such as, for example, one of the substrates discussed above was prepared. 5 g of Chitosan (HMW, Sigma MKBP1333V) was dissolved in a mixture of 460 mL distilled water and 40 mL 1M HCl. 10 mL of the viscous solution was poured into a Teflon petri dish and placed in a hood. After 24 h, the composition was dry to touch. It was then placed in a 50° C. oven under vacuum for 24 h. An equivalent procedure was used to prepare substrates from other materials. Details are given in Table A below.

TABLE A

| # | Agent | Supplier Lot # | Weight | Solvent | Result |
|---|---|---|---|---|---|
| 1 | Chitosan | Sigma MKBP1333V | 5 g | 460 mL water + 40 mL 1M HCl | Continuous film |
| 2 | PEG 20K | Fluka, 1303367 | 12.5 g | 25 mL Dichloromethane | No film |
| 3 | Polyvinylpyrollidone (PVP) | ISP Technologies, 0550149110 | 5 g | 15 mL water + 2 mL 1M HCl | Film |
| 4 | Jello | Sugar Free strawberry flavor | 0.350 g | 5 mL water | Film |
| 5 | PEG 20K + Jello | | 1:1 mix of 1 and 5 | | No Film |

Example 2

In another example, a hemostatic coated mesh substrate was prepared. A knitted multifilament mesh was taped down on a flat Teflon sheet. Prepared hemostat solutions described above were poured onto the mesh and spread using a Gardner Knife. The compositions were allowed to dry overnight in the hood and then at 50° C. under vacuum for 24 hours. Chitosan and PVP solutions and a 1:1 mixture of Chitosan and PVP were used to prepare hemostat coated meshes.

Figure 16:
FIG. 16 is a table showing results for Example 2.
Figure 16:
Figure 16:
Figure 16:
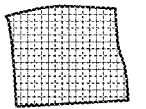
Figure 16:
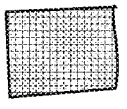
Figure 16:
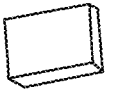

Hemostatic properties of the anchorage devices prepared in Examples 1 and 2 were observed. Water absorption was used as the initial screening test for hemostatic properties. A commercial hemostat Surgifoam was used as the control. Not wetted Surgifoam does not soak water easily, but wetted one works as a sponge. A piece of the hemostatic composition was placed on a flat Teflon surface. 3 drops of water were placed in the center of the composition and the time for water to absorb and the physical state of the hemostats were observed. Results are shown in FIG. 16.

Example 3

In another example, an anchorage device was prepared wherein the anchorage device had an active pharmaceutical ingredient, such as, for example, at least one antimicrobial agent was applied to a substrate, such as for example, a hemostatic mesh. A sheet of organic regenerated cellulose (ORC) made from multifilament fibers was stretched over a rectangular frame (10 inches×13 inches). This was coated with a 4% Weight by volume solution containing Rifampin, minocycline and tyrosine polyarylate (15:15:70 by weight) dissolved in THF:Methanol (9:1 VN) using an ultrasonic spraying machine (Ultrasonic Systems, Inc., Haverhill, Mass.). The coated mesh was dried under vacuum for 24 h at 50 C.

Example 4

In another example, an agent, such as, for example, at least one of the active pharmaceuticals discussed herein was selectively applied to a substrate of an anchorage device. Different patterns were created on an ORC sheet (made from multifilament fibers) by masking predetermined areas of the mesh with masking tape. The patterned sheet of ORC was stretched over a rectangular frame (10 inches×13 inches). This was coated with a 4% Weight by volume solution containing Rifampin, minocycline and tyrosine polyarylate (15:15:70 by weight) dissolved in THF:Methanol (9:1 VN) using an ultrasonic spraying machine (Ultrasonic Systems, Inc., Haverhill, Mass.). The coated mesh was dried under vacuum for 24 h at 50 C. The masking tape was peeled off to create meshes with the predetermined pattern.

Example 5

In another example, an anchorage device having a configuration of a pocket, pouch or envelope discussed above was prepared. Two sheets of the coated synthetic mesh were coated mesh placed one on top of the other and sealed and cut into the shape using an ultrasonic weld. The anvil used in the ultrasonic welding resulted in the formation of a pouch 2.5"×2.75" in size, sealed on approximately 3 and one-half sides. By changing the size and shape of the anvil, pouches of different sizes and shapes can be made.

Example 6

In another example, an agent, such as, for example, at least one of the hemostatic agents discussed herein was prepared to be applied to a substrate of an anchorage device, such as, for example, one of the substrates discussed herein. A 5% solution of chitosan (Aldrich, low molecular weight) was prepared as follows. 5 g of chitosan, 2.5 g of succinic acid were added to 100 mL of distilled water in a 250-mL glass jar containing a magnetic stir bar. The mixture was stirred at 500 rpm until a clear viscous solution was obtained.

Example 7

In another example, an agent, such as, for example, at least one of the hemostatic agents discussed herein was applied to a substrate of an anchorage device, such as, for example, one of the pockets, pouches or envelopes discussed herein. A piece of Tyvek (blown PTFE) film (size equal to that of the inner dimensions of the envelope) was placed within the envelope. The envelope was placed on a flat sheet of Teflon. About 10 mL of the hemostat solution was poured on the envelope and spread using a polypropylene rod. After drying for 24 hours under the hood, the envelope was removed, excess hemostat was trimmed off and the inner Teflon sleeve was removed. This resulted in the hemostatic agent being applied to one side of the envelope. That is, the other side of the envelope did not include the hemostatic agent.

Example 8

In another example, an agent, such as, for example, at least one of the hemostatic agents discussed herein was applied to a substrate of an anchorage device, such as, for example, one of the pockets, pouches or envelopes discussed herein. The envelope was mounted on a plastic mandrel, which was then dipped into the viscous solution of hemostat. Excess solution was allowed to drain. The mandrel was dried under vacuum at 80 C for 36 hours. After cooling, the envelope was removed from the mandrel. This resulted in the hemostatic agent being applied to both sides of the envelope.

Example 9

In another example, an anchorage device having a configuration of a pocket, pouch or envelope discussed above was prepared. The envelopes were made from one or more sheets comprising a hemostatic agent and a mesh material that is coated with an antibiotic, such as, for example at least one of the antibiotics discussed herein. The devices may be created from hemostatic sheets and synthetic mesh by fusing them using heat, ultrasonic energy or solvent, polymeric solutions or glue, as discussed below.

Figure 17:
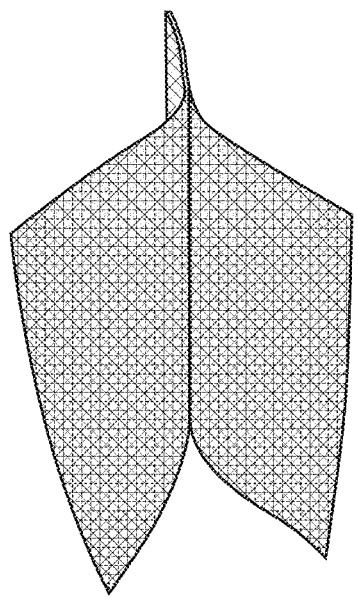
FIG. 17 is a perspective view of an anchorage device discussed in Example 9 in accordance with the principles of the present disclosure.
Figure 19:
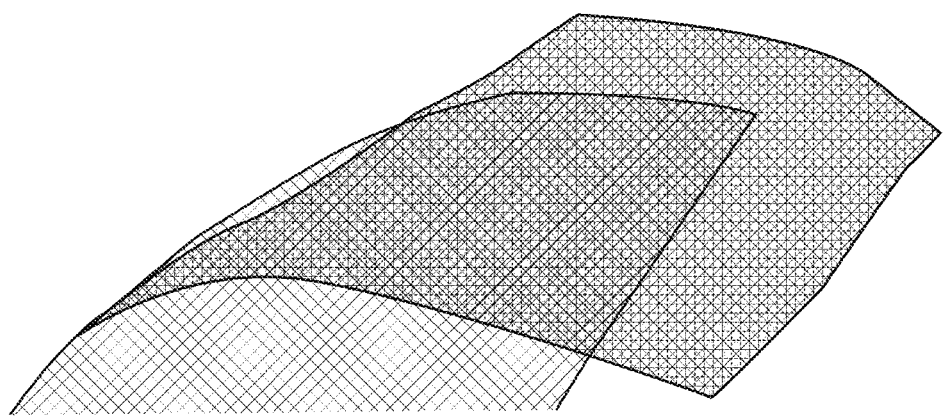
FIG. 19 is a perspective view of an anchorage device discussed in Example 9 in accordance with the principles of the present disclosure.
Figure 20:
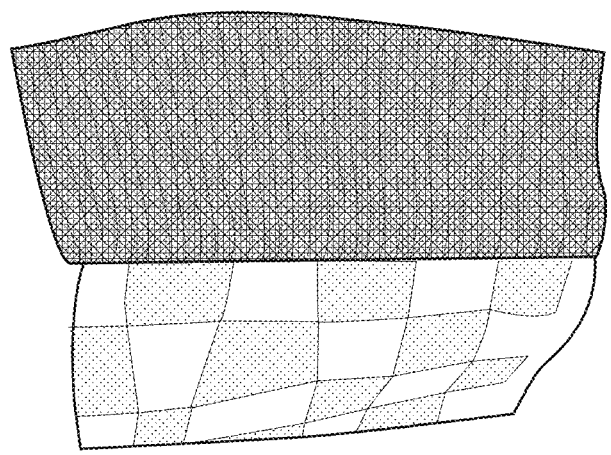
FIG. 20 is a perspective view of an anchorage device discussed in Example 9 in accordance with the principles of the present disclosure.

Heat:
    1. In one example, two sheets of ORC mesh coated with tyrosine polymer plus Rifampin and Minocycline were placed within the jaws of a PACWORLD bar sealer (using the following conditions: 7 Sec, 140 C, 80 psi. The sheets were fused together, as discussed herein, and shown in FIG. 17.
    2. In one example, one sheet of ORC mesh coated with tyrosine polymer, Rifampin and Minocycline and one sheet of biodegradable mesh made from glycolide, caprolactone and trimethylene carbonate coated with tyrosine polymer with Rifampin and Minocycline were placed within the jaws of a PACWORLD bar sealer (using the following conditions: 7 Sec, 140 C, 80 psi. The sheets were fused together, as discussed herein and shown in FIG. 18.
    3. In one example, one sheet of uncoated ORC mesh and one sheet of biodegradable mesh made from glycolide, caprolactone and trimethylene carbonate coated with tyrosine polymer with Rifampin and Minocycline were placed within the jaws of a PACWORLD bar sealer (using the following conditions: 7 Sec, 140 C, 80 psi. The sheets were fused together, as discussed herein and shown in FIG. 19.
    4. In one example, one sheet of coated ORC mesh coated with tyrosine polymer plus Rifampin and Minocycline in a pattern and one sheet of biodegradable mesh made from glycolide, caprolactone and trimethylene carbonate coated with tyrosine polymer with Rifampin and Minocycline in a pattern were placed within the jaws of a PACWORLD bar sealer (using the following conditions: 7 Sec, 140 C, 80 psi. The sheets were fused together, as discussed herein. The pattern on the ORC mesh sheet is shown in FIG. 20.

Solvent Based
    5. In one example, a solution of tyrosine polymer was placed between two sheets of uncoated ORC. The sheets were clamped together. After drying for 36 h under ambient conditions, it was further dried at 80 C for 24 hours. The sheets were fused together, as discussed herein.
    6. In one example, two sheets of polymer coated ORC were wetted with DMSO. The sheets were clamped together. After drying for 36 h under ambient conditions, it was further dried at 80 C for 24 hours. The sheets were fused together, as discussed herein.
    7. In one example, two sheets of polymer coated ORC was wetted with DMF. The sheets were clamped together. After drying for 36 h under ambient conditions, it was further dried at 80 C for 24 hours. The sheets were fused together, as discussed herein.

Adhesive
    8. In one example, a small amount of cyanoacrylate glue was placed between two sheets of uncoated ORC. The sheets were clamped together and dried at room temperature for 1 hour. The sheets were fused together, as discussed herein.

Sewing
    9. In one example, two sheets of ORC mesh coated with tyrosine polymer plus Rifampin and Minocycline were sewn together
    10. In one example, one sheet of ORC mesh coated with tyrosine polymer, Rifampin and Minocycline and one sheet of biodegradable mesh made from glycolide, caprolactone and trimethylene carbonate coated with tyrosine polymer with Rifampin and Minocycline were sewn together
    11. In one example, one sheet of uncoated ORC mesh and one sheet of biodegradable mesh made from glycolide, caprolactone and trimethylene carbonate coated with tyrosine polymer with Rifampin and Minocycline were sewn together
    12. In one example, one sheet of coated ORC mesh coated with tyrosine polymer plus Rifampin and Minocycline in a pattern and one sheet of biodegradable mesh made from glycolide, caprolactone and trimethylene carbonate coated with tyrosine polymer with Rifampin and Minocycline in a pattern were sewn together.
    13. In one example, one sheet of uncoated ORC mesh and one sheet of biodegradable film made from tyrosine polymer with Rifampin and Minocycline were sewn together.
    14. In one example, one sheet of ORC mesh coated with tyrosine polymer plus Rifampin and Minocycline and one sheet of biodegradable film made from tyrosine polymer with Rifampin and Minocycline were sewn together were sewn together.

Example 10

In another example, an agent, such as, for example, at least one of the hemostatic agents discussed herein was selectively applied to a substrate of an anchorage device. A sheet of biodegradable mesh made from glycolide, caprolactone and trimethylene carbonate coated with tyrosine polymer with Rifampin and Minocycline was fixed to a flat surface. Drops of a solution of Chitosan (5% w/v) in water containing succinic acid was applied to the mesh using a syringe. The mesh was dried overnight at room temperature and then at 80° C. under vacuum for 24 h.

Example 11

In another example, agents, such as, for example, at least one of the hemostatic agents discussed herein and at least one of the active pharmaceutical ingredients discussed herein were selectively applied to a substrate of an anchorage device. A 4% Weight by volume solution containing Rifampin, minocycline and tyrosine polyarylate (15:15:70 by weight) dissolved in THF:Methanol (9:1 V/V) was first prepared. Fine particles of a suitable hemostatic agent were suspended in this mixture and the suspension was sprayed onto a suitable mesh substrate. After drying under ambient condition until the coating was dry to the touch, the mesh was dried in a vacuum oven at 80° C. for 24 to 72 hours. The hemostatic agents can be selected from any of the hemostatic agents discussed herein and/or tranexamic acid, amino caproic acid (e.g., epsilon amino caproic acid), aprotinin, natural serine protease inhibitors, or polymers such as ORC or chitosan or other polysaccharides. In some embodiments, the hemostatic agents can include Arista AH hemostat and a desiccant. In some embodiments, the Arista AH hemostat is a hydrophilic, flowable, sterile, fine, dry white powder made by crosslinking purified plant starch through a proprietary process into Microporous Polysaccharide Hemispheres (MPH). In some embodiments, the hemostatic agents can include those discussed by Barnard J, Millner R, "A Review of Topical Hemostatic Agents for Use in Cardiac Surgery," Ann Thorac Surg. 2009, 88: 1377-1383. 10.1016, which is incorporated herein by reference, in its entirety. In some embodiments, the hemostatic agents can include those discussed by Jill Henley, Jerry D. Brewer, "Newer Hemostatic Agents Used in the Practice of Dermatologic Surgery," Dermatology Research and Practice 2013, 1-15, which is incorporated herein by reference, in its entirety. In some embodiments, the hemostatic agents can include those discussed by F. I. Broekema, W. Van Oeveren, J. Zuidema, S. H. Visscher, and R. R. M. Bos, "In vitro analysis of polyurethane foam as a topical hemostatic agent," Journal of Materials Science, vol. 22, no. 4, pp. 1081-1086, 2011, which is incorporated herein by reference, in its entirety.

Example 12

In another example, anchorage devices having a substrate, such as, for example, one of the substrates discussed above were prepared wherein the substrate was made from fibers that include a hemostatic agent, such as, for example, at least one of the hemostatic agents discussed herein, and fibers that do not include a hemostatic agent. In one example, the fibers that include the hemostatic agent are made from an aqueous solution that include the hemostatic agent(s). In some embodiments, an active pharmaceutical ingredient is added to the aqueous solution. In one example, the fibers that do not include the hemostatic agent are coextruded with an active pharmaceutical ingredient, such as, for example, at least one of the active pharmaceutical ingredients discussed herein. The fibers are swelled in some solvent containing the API, such as, for example, polyurethane or silicone in THF. The fibers that include the hemostatic agent and the fibers that do not include the hemostatic agent are dried, and the dried fibers are used to form a mesh. In some embodiments, the fibers that include the hemostatic agent are made as discussed by Pillai, C. K. S.; Paul, W.; Sharma, C. P. Chitin and chitosan polymers: Chemistry, solubility and fiber formation. Prog. Polym. Sci. 2009, 34, 641-678, which is incorporated herein by reference, in its entirety.

Example 13

In another example, an agent, such as, for example, at least one of the active pharmaceuticals discussed herein was applied to a substrate of an anchorage device such that the agent eluted or released from the substrate at a selected rate. The substrate was made from various combinations of Glycoprene®, ORC, polymer-coated Glycoprene® (e.g., one of the tyrosine-derived polymers discussed herein), and polymer-coated ORC (e.g., one of the tyrosine-derived polymers discussed herein). The samples were weighed in 20 mL scintillation vials and then immersed in 20 mL of phosphate buffered saline (pH 7.4). The vials were allowed to shake at 120 rpm in an incubator at 37° C. At various subsequent time points, 1 mL of the buffer was removed for analysis by UPLC. At each time point after 1 mL was removed, the buffer was decanted. The vials were replenished with fresh buffer and returned to the incubator. The volume of fresh buffer was gradually reduced from the initial 20 mL to 10 mL, 5 mL, and 2 mL in order to maintain a concentration that can be detected by UPLC.

Samples of coated ORC and coated Glycoprene® were weighed in 20 mL scintillation vials. Samples were initially dissolved in DMSO and allowed to shake for at least 15 minutes. Then, MeOH was added and vials were allowed to shake for another minimum of 15 minutes. One (1) mL of each solution was then filtered through a 0.45 micron PTFE filter and loaded onto the UPLC for analysis. Results below are reported as a cumulative % released against time.

Figure 21:
FIG. 21 is a table showing results for Example 13.
Figure 21:
Figure 21:
Figure 21:
Figure 21:
Figure 21:
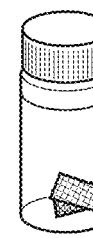
Figure 21:
Figure 21:
Figure 21:
Figure 21:
Figure 21:
Figure 21:
Figure 21:
Figure 21:
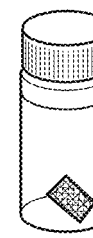
Figure 21:
Figure 21:
Figure 21:
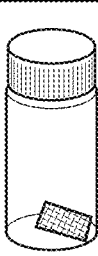
Figure 21:
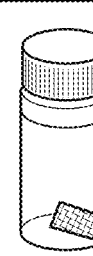
Figure 21:
Figure 21:
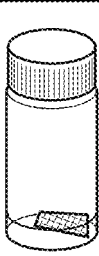

Substrates, such as, for example, the substrates discussed herein, were prepared, as discussed herein, to include coatings (e.g., polymers) that elute an active pharmaceutical ingredient, such as, for example, at least one of the active pharmaceutical ingredients discussed herein, at different rates. Ten samples were produced (Samples 1-6 and 9-12), as shown in FIG. 21. In the data provided below, "Tyrx" or "TYRX" refers to a degradable polymer, and in particular, to one or more of the tyrosine-derived polymers discussed herein, wherein the polymer includes at least one active pharmaceutical ingredient.

Figure 22:
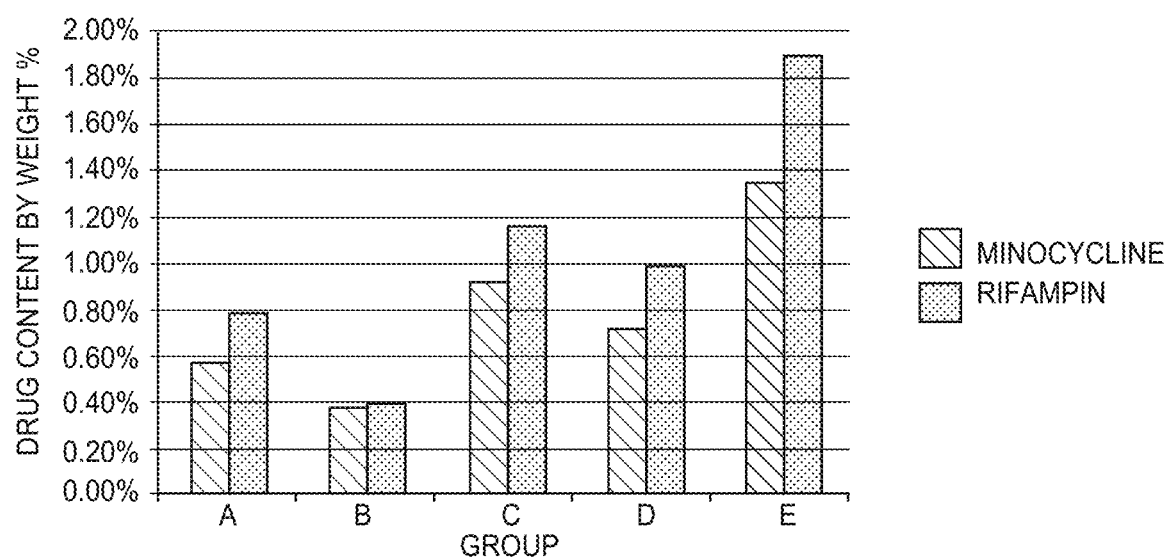
FIG. 22 is a graph showing drug content by weight of anchorages device discussed in Example 13.

The active pharmaceutical ingredient(s) or drug(s) in each of Samples 1-6 and 9-12 is shown in FIG. 22. Further details regarding the substrates used in Samples 1-6 and 9-12 are provided below.

|  | Sample | Weight (mg) | | | | Sample |
|---|---|---|---|---|---|---|
|  |  | Glycoprene | AIGIS-R | ORC | TYRX-coated ORC |  |
| Drug Elution | 1 | 16.1 | — | — | 60.4 | 1 |
|  | 2 | 13.7 | — | — | 57.7 | 2 |
|  | 3 | — | 14.4 | 56.3 | — | 3 |
|  | 4 | — | 14.9 | 56.1 | — | 4 |
|  | 5 | — | 14.7 | — | 63.6 | 5 |
|  | 6 | — | 13.3 | — | 59.1 | 6 |
|  | 9 | — | — | — | 49.3 | 9 |
|  | 10 | — | — | — | 53.2 | 10 |
|  | 11 | — | 10.3 | — | — | 11 |
|  | 12 | — | 11.5 | — | — | 12 |
| Drug Content | 13 | — | — | — | 113.9 |  |
|  | 14 | — | — | — | 118.1 |  |
|  | 15 | — | 87.8 | — | — |  |
|  | 16 | — | 95.6 | — | — |  |

AIGIS-R refers to a resorbable mesh substrate that is coated with a polymer, such as, for example, one of the tyrosine-derived polymers discussed herein, wherein the polymer includes at least one active pharmaceutical ingredient, as shown below. In the samples that include Glycoprene®, the Glycoprene® is a mesh that forms the substrate.

Figure 23A:
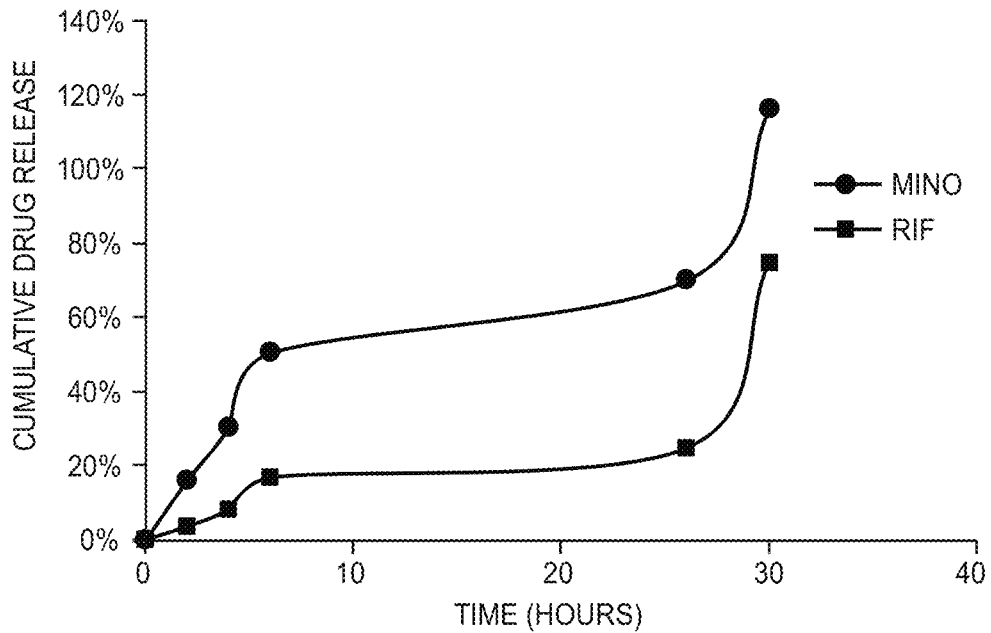
FIG. 23A is a graph showing elution profiles of Samples 1 and 2 discussed in Example 13.
Figure 23B:
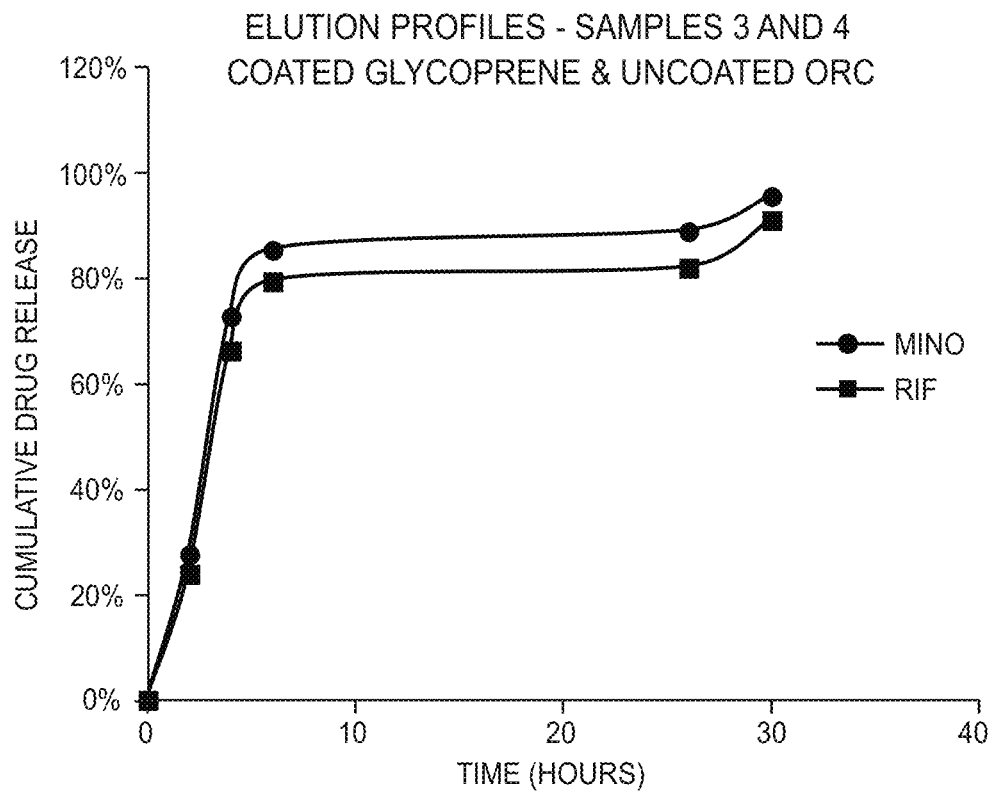
FIG. 23B is a graph showing elution profiles of Samples 3 and 4 discussed in Example 13.
Figure 23C:
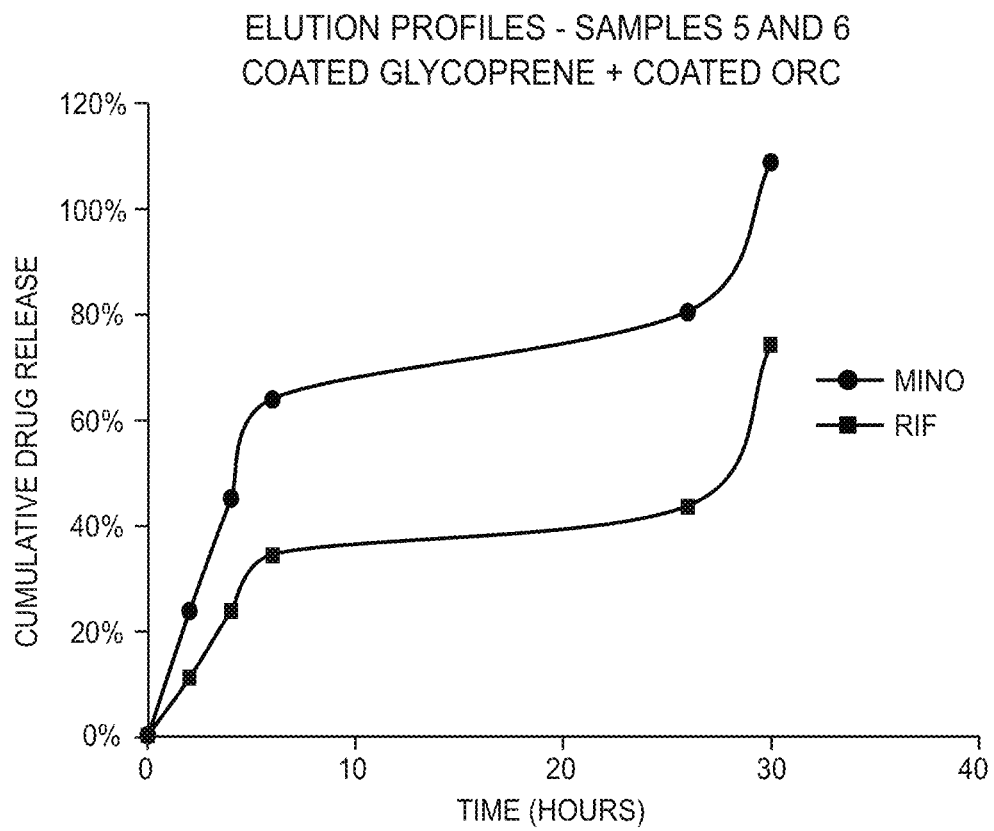
FIG. 23C is a graph showing elution profiles of Samples 5 and 6 discussed in Example 13.
Figure 23D:
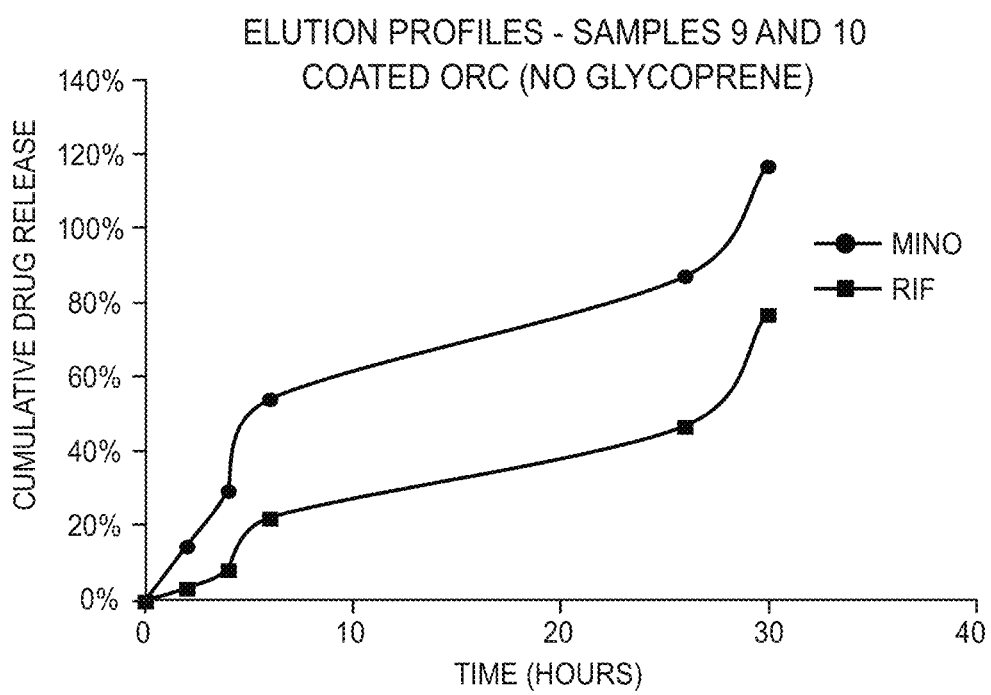
FIG. 23D is a graph showing elution profiles of Samples 9 and 10 discussed in Example 13.
Figure 23E:
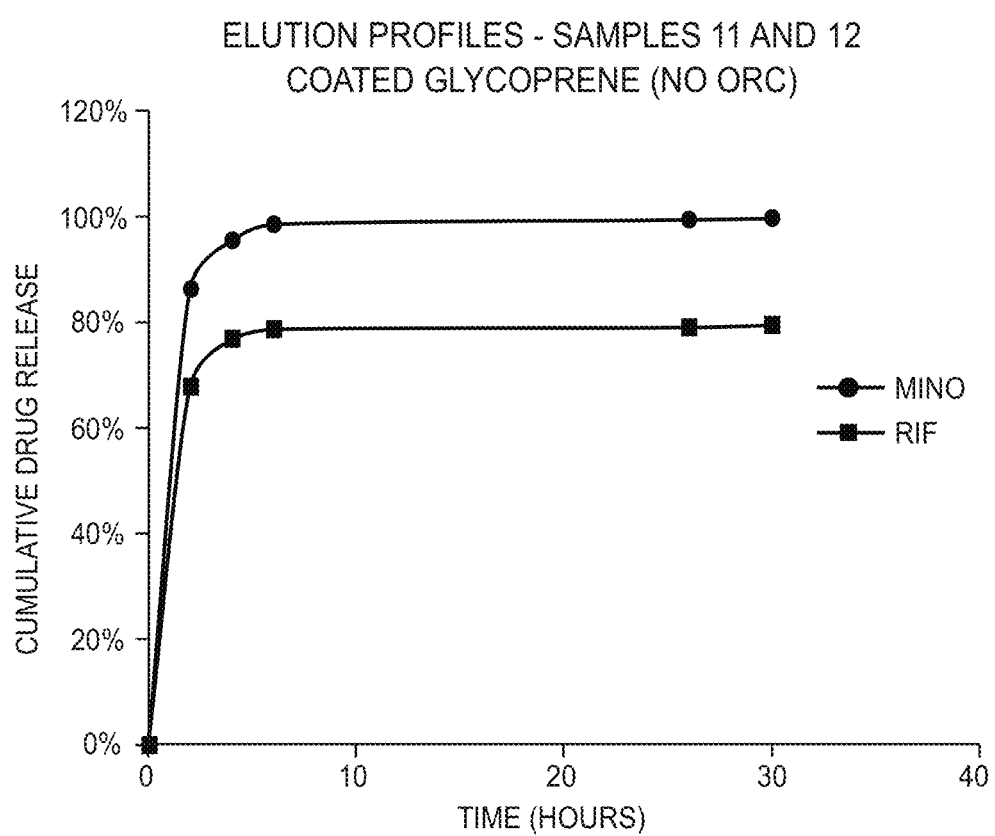
FIG. 23E is a graph showing elution profiles of Samples 11 and 12 discussed in Example 13.
Figure 23L:
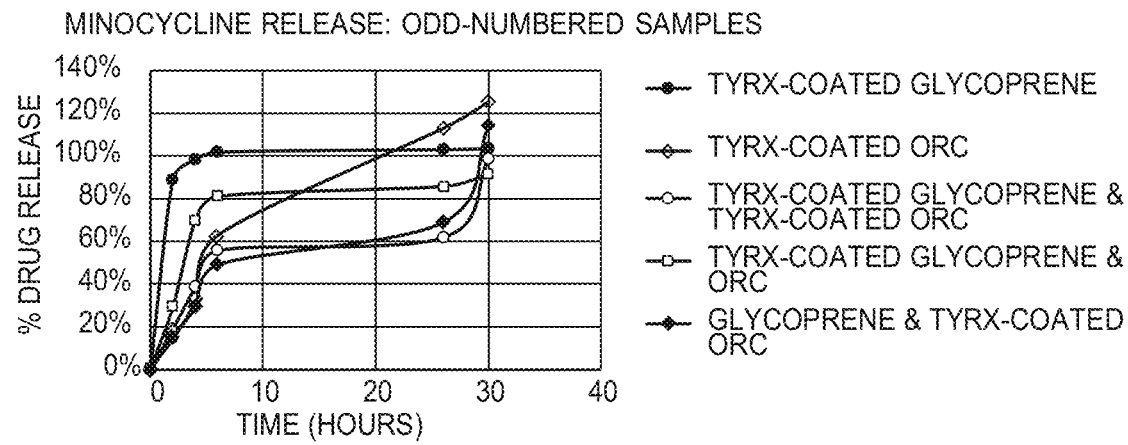
FIG. 23L includes a graph showing drug release profiles for samples discussed in Example 13.
Figure 23M:
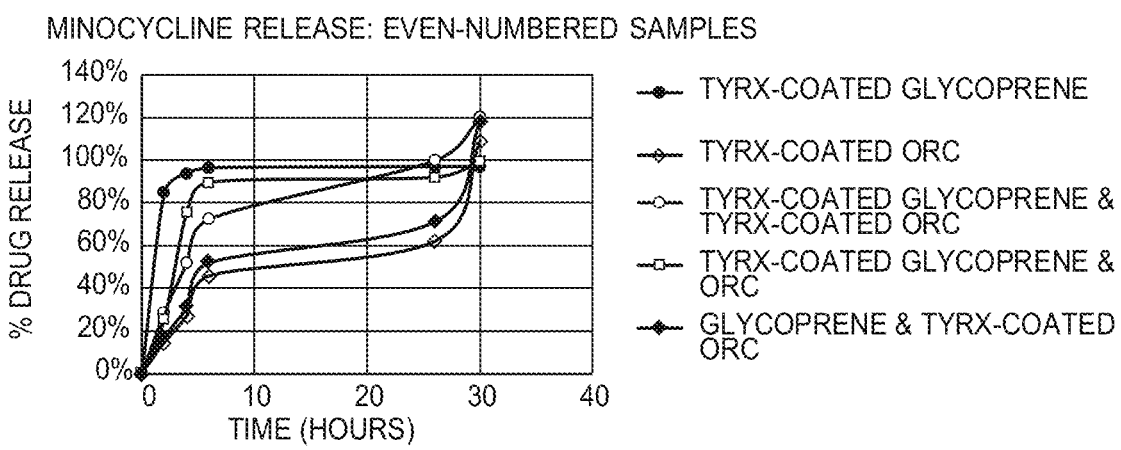
FIG. 23M includes a graph showing drug release profiles for samples discussed in Example 13.
Figure 23N:
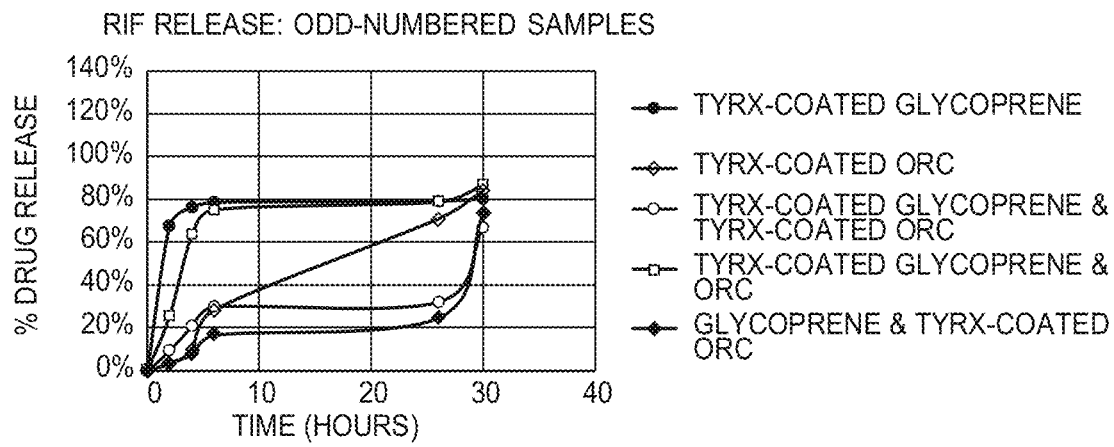
FIG. 23N includes a graph showing drug release profiles for samples discussed in Example 13.
Figure 23O:
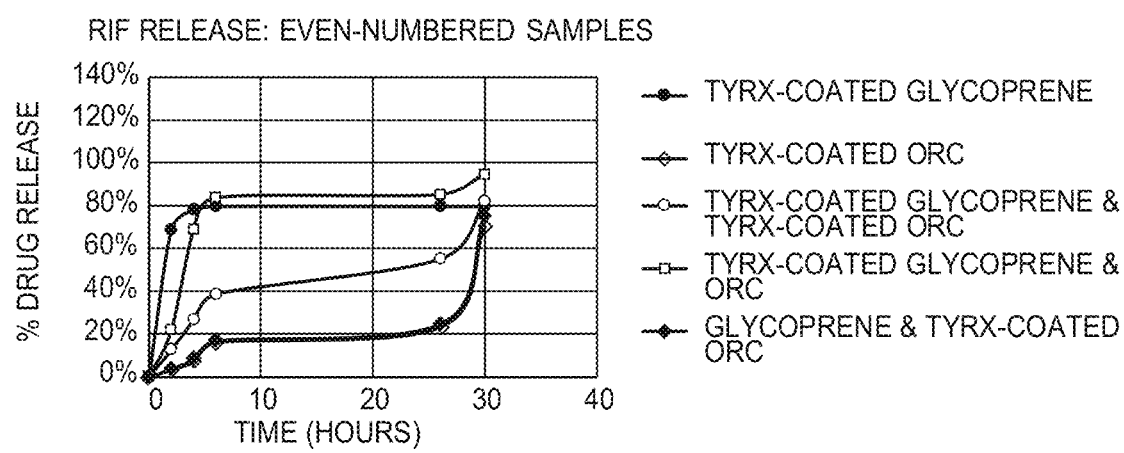
FIG. 23O includes a graph showing drug release profiles for samples discussed in Example 13.
Figure 23P:
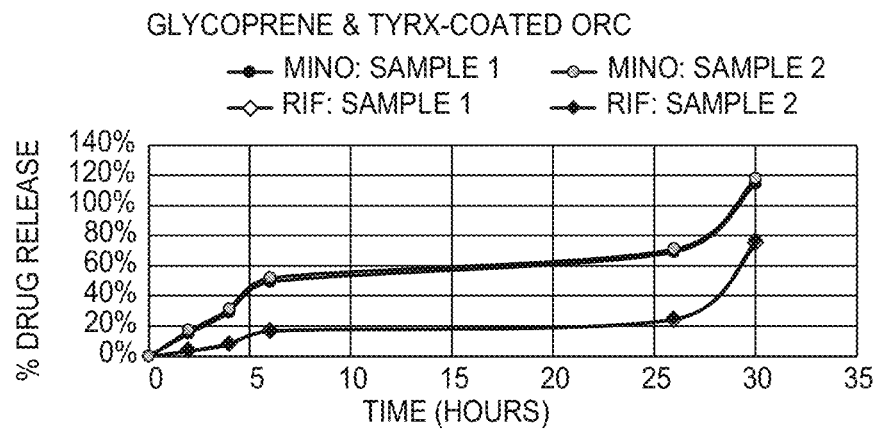
FIG. 23P includes a graph showing drug release profiles for samples discussed in Example 13.
Figure 23Q:
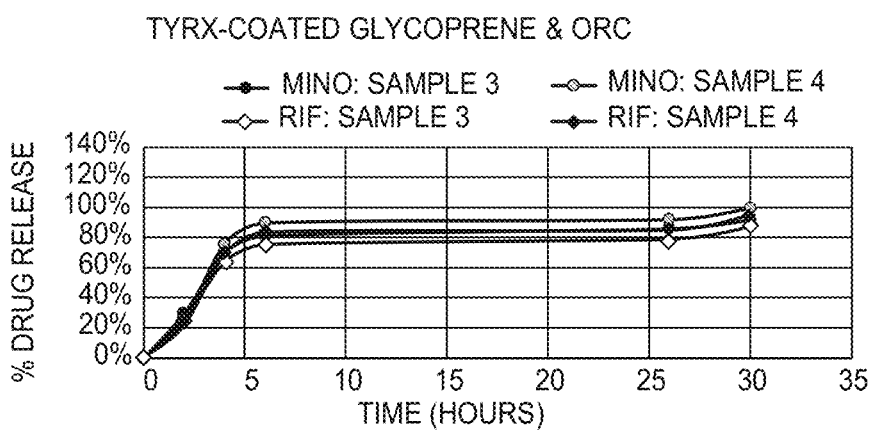
FIG. 23Q includes a graph showing drug release profiles for samples discussed in Example 13.
Figure 23R:
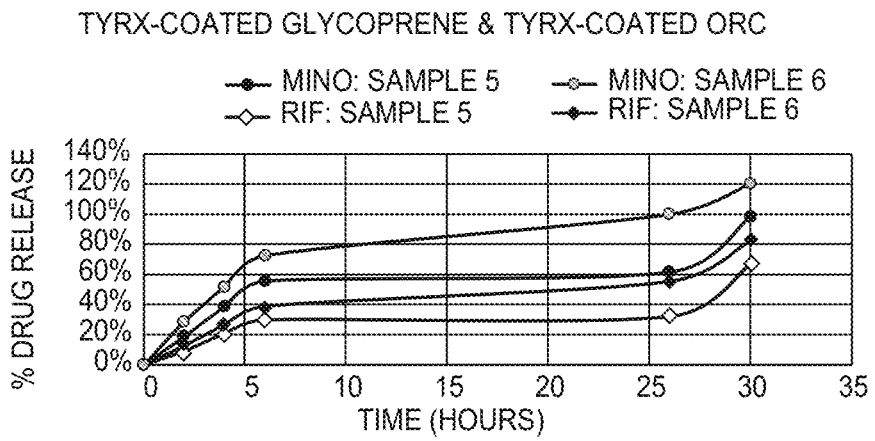
FIG. 23R includes a graph showing drug release profiles for samples discussed in Example 13.
Figure 23S:
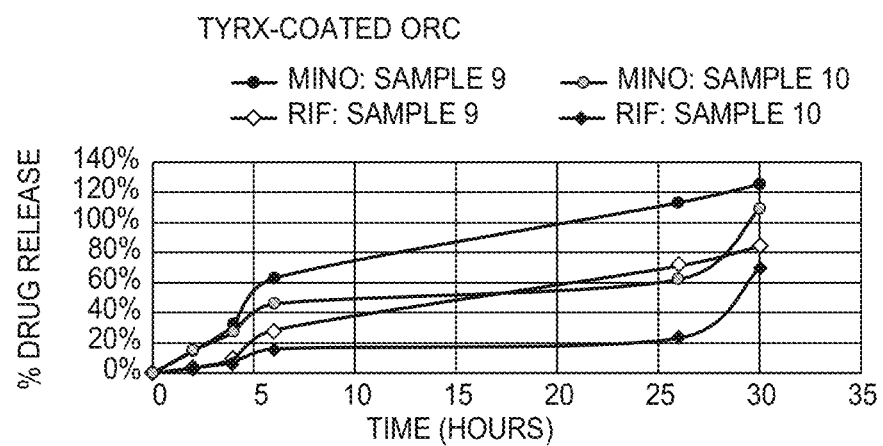
FIG. 23S includes a graph showing drug release profiles for samples discussed in Example 13.
Figure 23T:
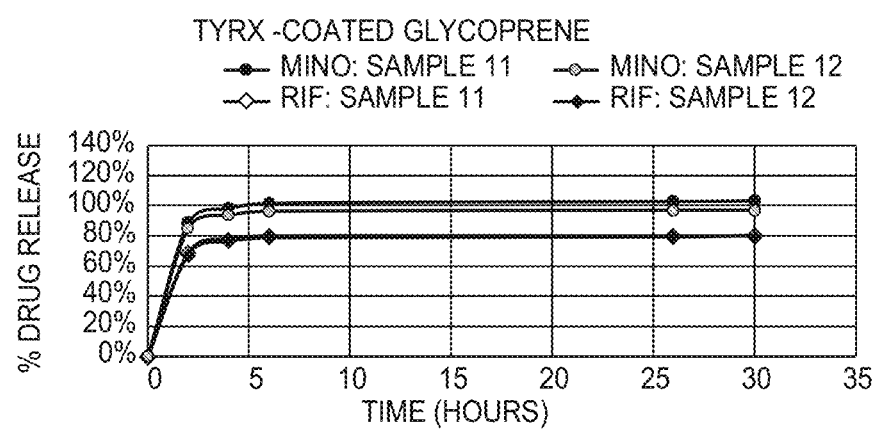
FIG. 23T includes a graph showing drug release profiles for samples discussed in Example 13.

The elution rates of the active pharmaceutical ingredients in Samples 1-6 and 9-12 are shown in the elution profiles in FIGS. 23A-23T.

In this example, different substrates were examined to test and compare the elution profiles of the different substrates to determine the effect, if any, of combining polymer-coated substrates with uncoated substrates.

When uncoated Glycoprene® was added to coated ORC in samples 1 and 2, both minocycline and rifampin releases were below 20% after 2 hours. By 24 hours, minocycline release was above 60%, and rifampin release was over 20%. Minocycline and rifampin releases continued to increase between 24 and 30 hours.

With the addition of uncoated ORC to coated Glycoprene® in samples 3 and 4, more than 20% minocycline and 20% rifampin was released after 2 hours. After 6 hours, minocycline release was over 80% while rifampin release was over 60%.

Samples 5 and 6 consisted of both coated Glycoprene® and coated ORC. After 2 hours, minocycline release was over 20% while rifampin release was around 50%. By 6 hours, more than 60% of minocycline was released, and more than 20% of rifampin was released. After 24 hours, rifampin release was approximately 40% while minocycline release was over 70%. Minocycline and rifampin releases continued to increase between 24 and 30 hours.

Minocycline and rifampin elution from samples 9 and 10 (coated ORC) was below 20% after 2 hours. After 24 hours, minocycline release was over 60%, while rifampin release was over 20%. Minocycline and rifampin releases continued to increase between 24 and 30 hours.

For samples 11 and 12 of coated Glycoprene®, more than 80% minocycline and more than 60% rifampin was released in 2 hours. Minocycline and rifampin release rate gradually increased until it leveled off after 6 hours.

In samples 1-6 and 9-10 after 2 hours' immersion in PBS, the ORC component can be visually observed to be swollen.

Example 14

Figure 24:
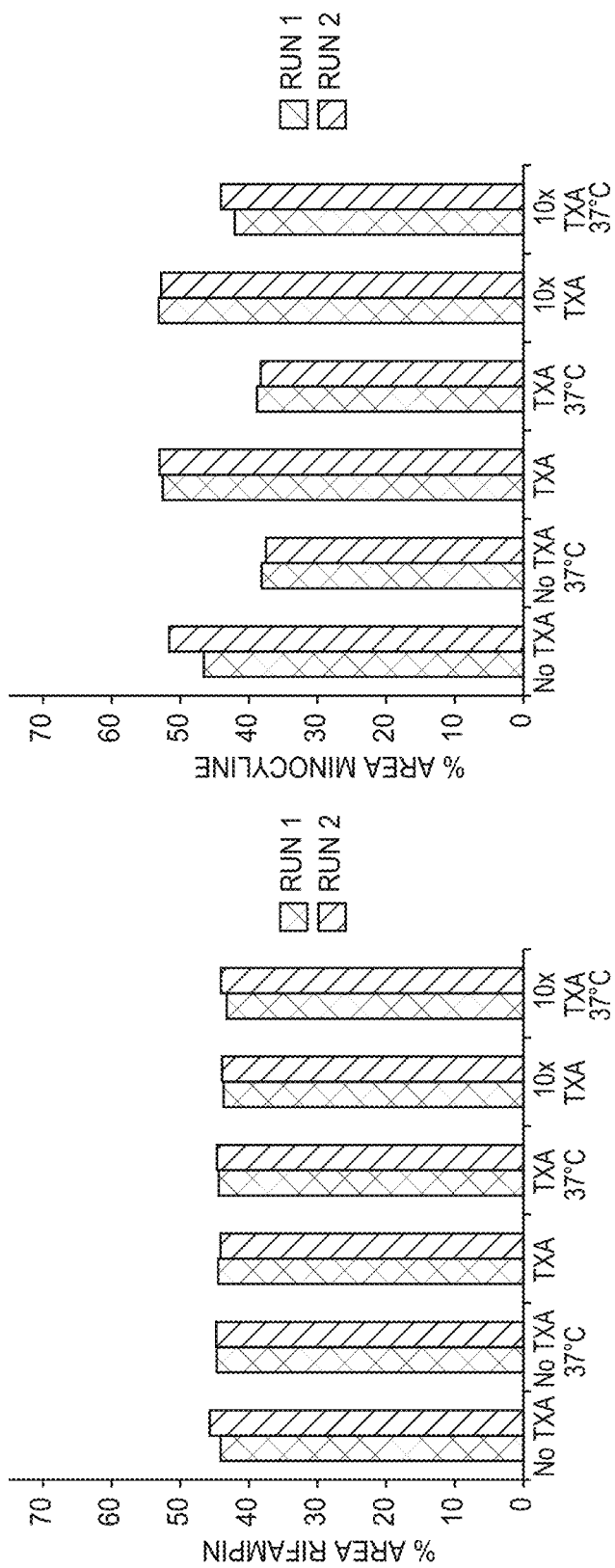
FIG. 24 includes graphs showing results discussed in Example 14.

To determine the stability of active pharmaceutical ingredients, such as, for example, one or more of active pharmaceutical ingredients 26 when combined with a hemostatic agent, such as, for example, one or more of hemostatic agents 24, mixtures of rifampin and minocycline were prepared in phosphate-buffered saline (PBS) with and without tranexamic acid (TXA). The mixtures were tested both at room temperature (RT) (about 23° C.) and at 37° C. As shown in FIG. 24, mixtures of rifampin and minocycline in PBS with and without tranexamic acid have substantially the same percentage area of rifampin and minocycline, thus indicating that tranexamic acid does not negatively affect the stability of rifampin and minocycline. In particular, the percentage area of rifampin was substantially the same for mixtures of rifampin and minocycline in PBS with and without tranexamic acid, regardless of the temperature; the percentage area minocycline was substantially the same for mixtures of rifampin and minocycline in PBS with and without tranexamic acid when the mixtures were at the same temperature.

Example 15

Figure 25:
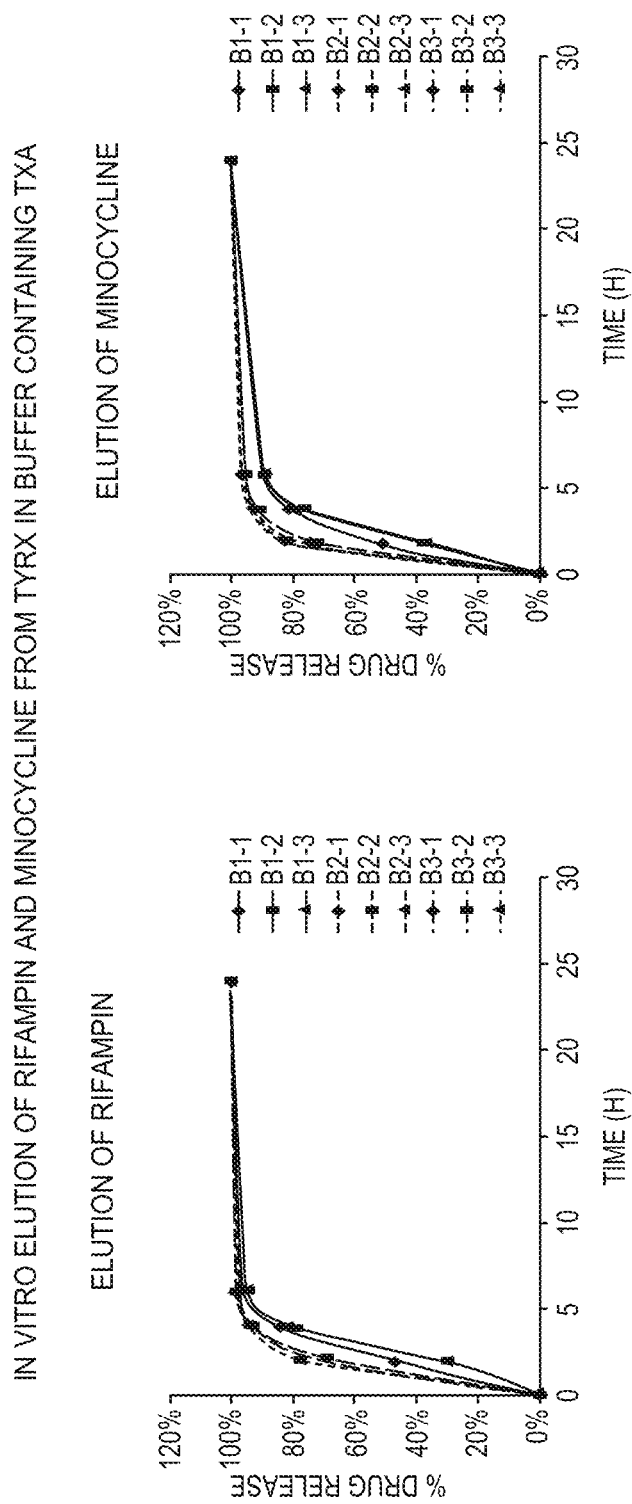
FIG. 25 includes graphs showing results discussed in Example 15.

To determine the elution of active pharmaceutical ingredients, such as, for example, one or more of active pharmaceutical ingredients 26 from a polymer, such as, for example, one of the polymers discussed herein, in vitro when the active pharmaceutical ingredients are combined with a hemostatic agent, such as, for example, one or more of hemostatic agents 24, in vitro elution of rifampin and minocycline from polymers in the p22-27.5 family containing different amounts of tranexamic acid was evaluated in a PBS buffer over 25 hours. B1=PBS pH 7.4; B2=PBS, pH 7.4+TXA (0.05 mg/mL); B3=PBS, pH 7.4+TXA (5 mg/mL). The elution rates for rifampin and minocycline are shown in FIG. 25. As shown in FIG. 25, the elution rates of rifampin and minocycline were not affected by the presence of TXA in the release media.

Example 16

Figure 26:
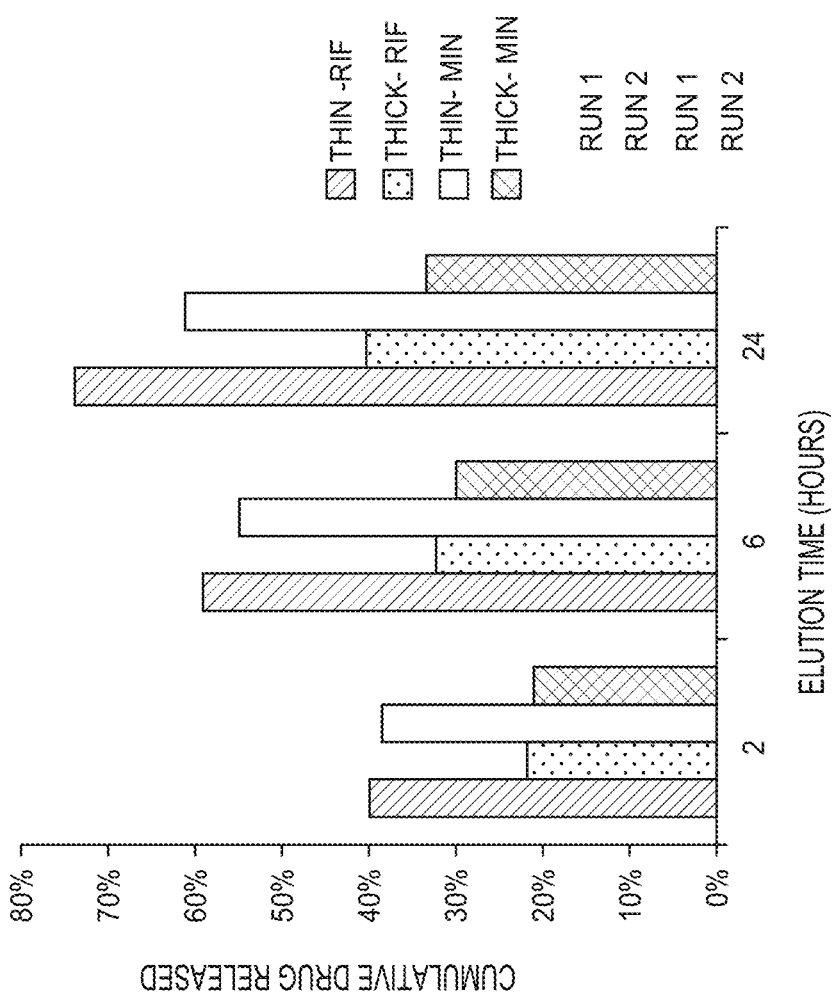
FIG. 26 is a graph showing results discussed in Example 16.

To determine the sustained release of active pharmaceutical ingredients, such as, for example, one or more of active pharmaceutical ingredients 26 from a polymer, such as, for example, one of the polymers discussed herein, when the active pharmaceutical ingredients are combined with a hemostatic agent, such as, for example, one or more of hemostatic agents 24, thin and thick solvent cast films containing rifampin (Rif) and tranexamic acid were prepared. Thin and thick solvent cast films containing minocycline (Min) and tranexamic acid were also prepared. The tranexamic acid phase was separated in each of the films. Thin films had a thickness of about 30 microns and thick films had a thickness of about 400 microns. Elution of rifampin and minocycline was measured over about 30 hours. The percentage of rifampin and minocycline released at 2 hours, 6 hours and 24 hours was recorded. As shown in FIG. 26, the thin films released rifampin and minocycline more quickly than the thick films at the same time intervals. However, for each set of films (thick and thin), rifampin and minocycline were shown to elute at similar rates.

Example 17

Figure 31:
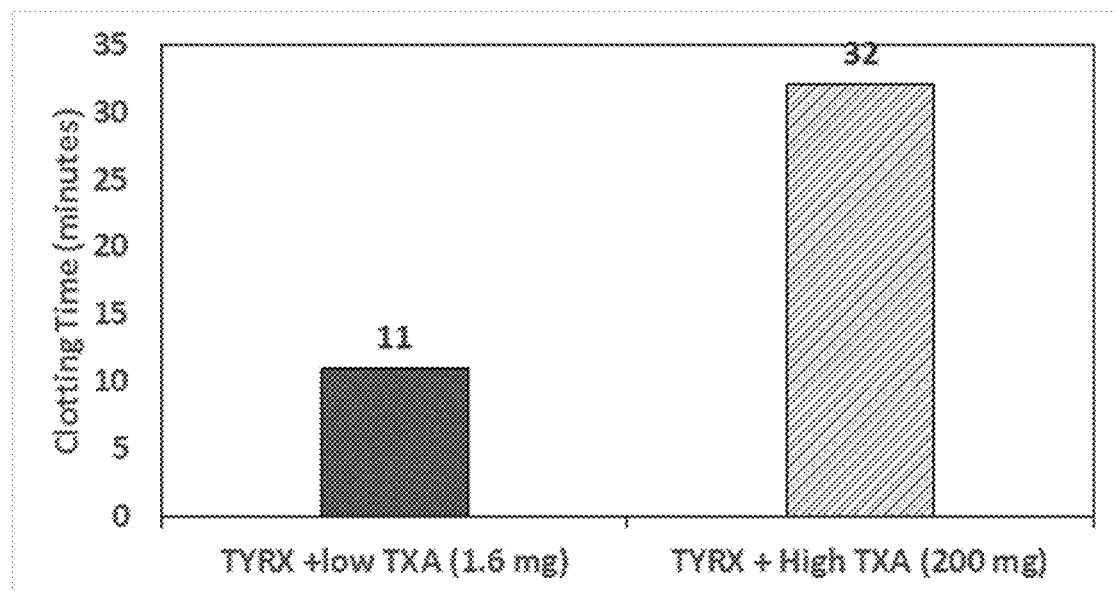
FIG. 31 is a graph showing results discussed in Example 17.

Tests were conducted to compare the time required to induce blood clotting in vitro when different amounts of hemostatic agent is administered in the presence of TYRX (degradable mesh coated with P22-27.5 containing rifampin and minocycline), as shown in FIG. 40. Clotting time was increased when higher amounts of TXA was present (1.6 mg TXA vs 200 mg of TXA), as shown in FIG. 31.

Example 18

Figures 27, 28:
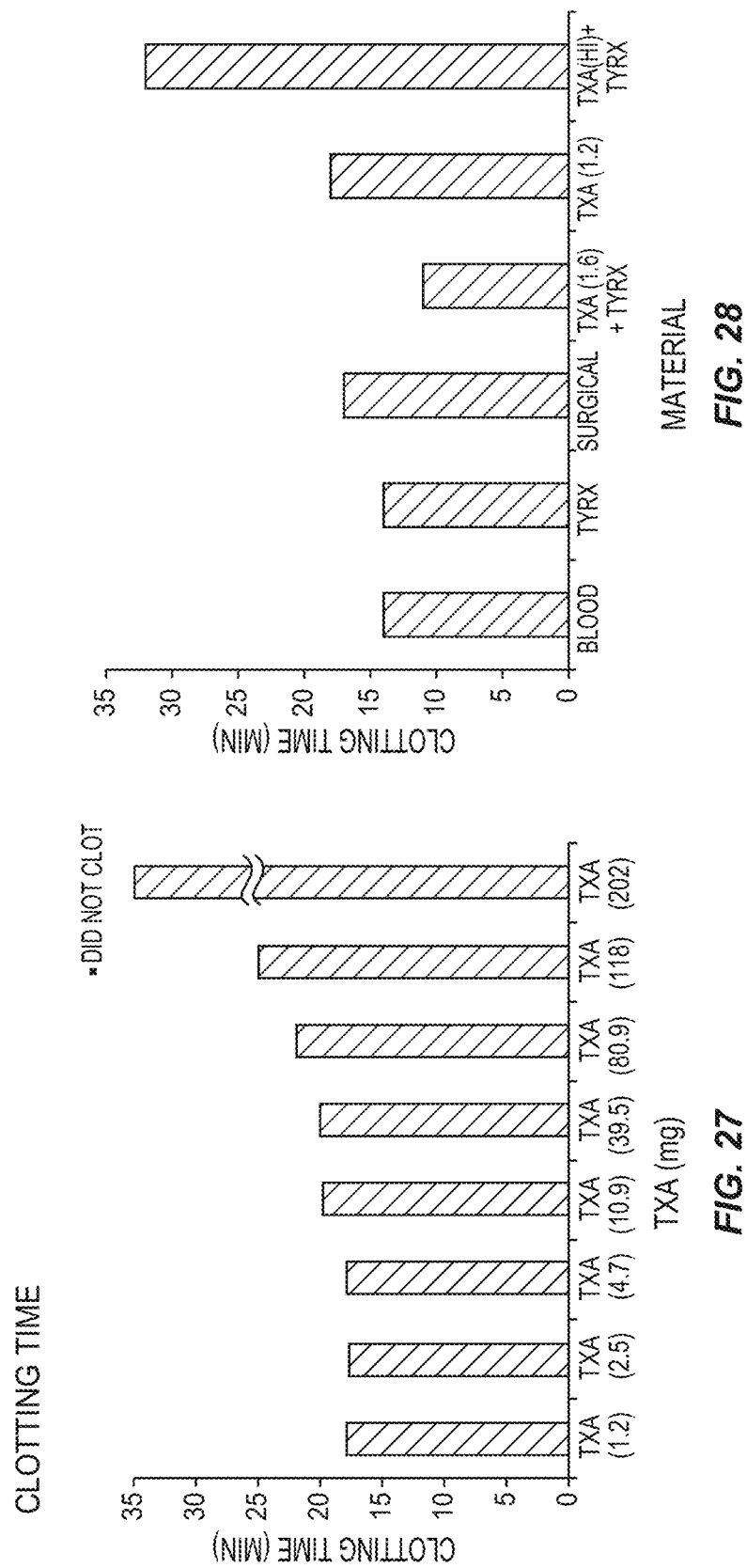
FIG. 27 is a graph showing results discussed in Example 17.
FIG. 28 is a graph showing results discussed in Example 18.

Tests were conducted to compare the time required for different hemostatic agents to induce blood clotting in vitro versus the time required to induce blood clotting in vitro when no hemostatic agent is administered. In particular, the time required to induce blood clotting was plotted for blood alone, TYRX, Surgicel, TYRX with 1.6 mg of TXA, 1.2 mg of TXA alone and TYRX with 200 mg of TXA. In trhis example, TYRX refers to a Glycoprene mesh that is coated with P22-27.5 (a polymer in the P22-X family) containing Rifampin and Minocycline. As shown in FIG. 28, blood alone and TYRX were both effective to induce blood clotting in about 14 minutes; Surgicel was effective to induce blood clotting in about 17 minutes; TYRX with 1.6 mg of TXA was effective to induce blood clotting in about 12 minutes; 1.2 mg of TXA alone was effective to induce blood clotting in about 19 minutes; and the p22-27.5 polymer having 200 mg of TXA was effective to induce blood clotting in about 32 minutes, thus indicating that TYRX with low amount of TXA (1.6 mg) may induce blood clotting better than TYRX with 200 mg TXA.

Example 19

Figure 29:
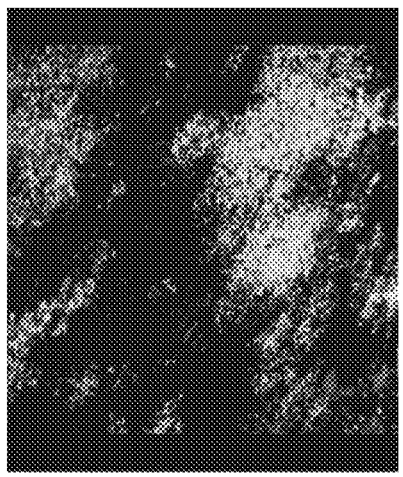
FIG. 29 includes slides showing results discussed in Example 19.
Figure 29:
Figure 29:
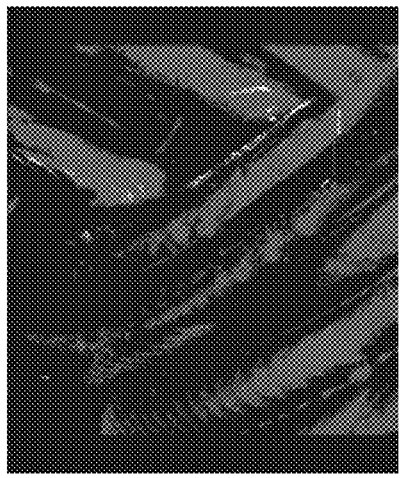

To determine the impact, if any, of a hemostatic agent, such as, for example, one or more of hemostatic agents 24 on bacterial attachment, three samples were prepared. The first sample included a TYRX polymer in the p22-xx family (P22-27.5-TYRX); the second sample included TYRX and tranexamic acid (TYRX+TXA); and the third sample included an extracellular matrix (ECM) to be used as a control. In this example, TYRX refers to a glycoprene mesh that is coated with P22-27.5 (a polymer in the P22-X family) containing rifampin and minocycline. The samples were each suspended in 3 mL of a Brain Heart Infusion (BHI) medium at 37° C. for 24 hours. The samples were each inoculated with 2×Colony Forming Units (CFU)/mL of a clinical strain of Methicillin-resistant Staphylococcus aureus (MRSA). After 24 hours, each of the samples was rinsed twice and bacterial attachment was visualized by Live/Dead staining and imaged with Leica DM RXE microscope attached to a TCS SP2 AOBS confocal system (Leica Microsystems, Exton, Pa.). As shown in FIG. 29, the TYRX and TYRX+TXA samples exhibited less bacterial attachment than ECM control.

Example 20—Chitosan Solutions for Preparing Films 1 gram of Chitosan (Sigma) was added to 100 mL of Aqueous Acetic acid (1% Acetic acid). The mixture was stirred using a magnetic stir bar until no solids remained.

Films were cast by pouring on 10 mL of the chitosan solution onto a TEFLON sheet. The solution was covered with a Petri dish dried in a ventilated hood 24 hrs. The Petri dish was removed and the films dried for an addition 72 hrs. A transparent film was obtained.

50 mg of Tranexamic acid was added to 10 g of the chitosan solution prepared as described above in a 20-mL scintillation vial. The vial was capped and placed on a shaker. The contents were shaken for 1 hr, when all the TXA had dissolved.

Films were cast by pouring on to a TEFLON sheet. The solution was covered with a Petri dish dried in a ventilated hood 24 hrs. The Petri dish was removed and the films dried for an addition 72 hrs. A transparent film was obtained.

50 mg of Tranexamic acid, 50 mg of Rifampin, 50 mg of Minocycline-HCL was added to 10 g of the chitosan solution prepared as described above in a 20-mL scintillation vial. The vial was capped and placed on a shaker. The contents were shaken for 1 hr, when all the drugs had had dissolved.

Films were cast by pouring on to a TEFLON sheet. The solution was covered with a Petri dish dried in a ventilated hood 24 hrs. The Petri dish was removed and the films dried for an addition 72 hrs. A transparent red film was obtained.

Two kinds of meshes were used in these experiments—a monofilament mesh of polypropylene (non-absorbable) and a multifilament absorbable mesh (GLYCOPRENE II), which is made from glycolide, caprolactone and trimethylene carbonate.

Strips of mesh approximately 1 cm×3 cm were hand dipped into the solutions of chitosan, Chitosan+Tranexamic acid and Chitosan+Tranexamic acid+Rifampin+Minocycline. HCl. These solutions were prepared as described above. Excess solution was removed using Kim wipes and wet strips were hung to dry in a hood. The coated meshes were dry to the touch after overnight drying.

Example 21—Avoiding Crystallization in Films

To assess how to avoid crystallization in films, four samples were prepared—sample J, sample L, sample B2 and sample F2. Sample J includes a polymer in the p22-xx family (P22-27.5-TYRX), rifampin, minocycline and tranexamic acid. Sample L includes a polymer in the p22-xx family (P22-27.5-TYRX), rifampin, minocycline, tranexamic acid and water. Sample B2 includes a polymer in the p22-xx family (P22-27.5-TYRX) and tranexamic acid. Sample F2 includes a polymer in the p22-xx family (P22-27.5-TYRX), tranexamic acid and water.

The samples were imaged using a digital microscope under a variety of illumination conditions and magnifications of 50×, 100×, and 200×. Transmitted crossed-polarized illumination highlighted anisotropic, apparently crystalline features in several films, as shown in FIG. 38.

Figure 30:
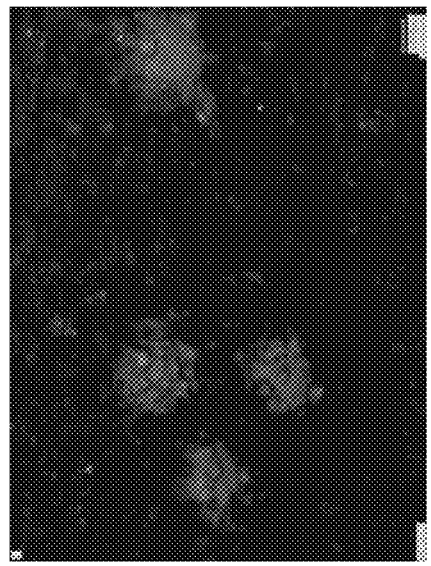
FIG. 30 includes images of samples discussed in Example 21.
Figure 30:
Figure 30:
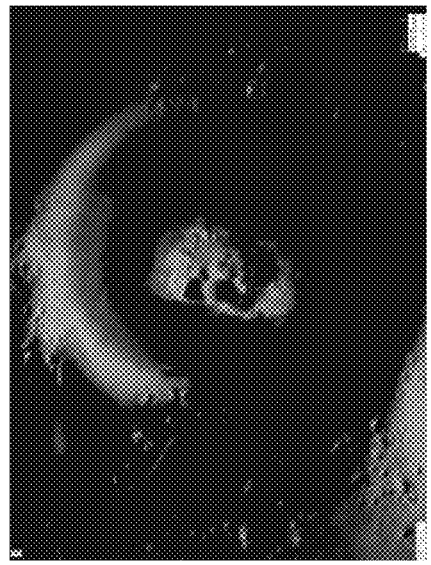
Figure 30:
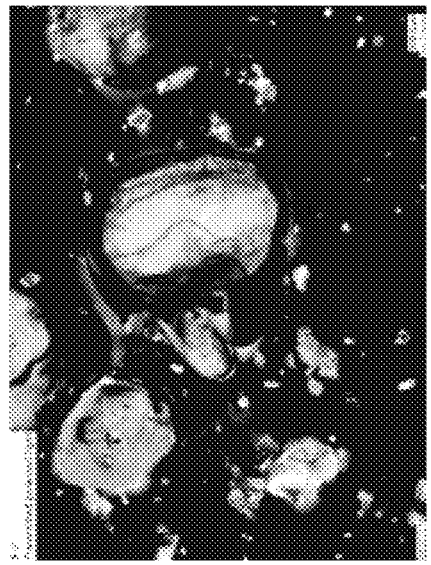

Transmitted crossed-polarized illumination highlighted anisotropic, apparently crystalline features in films containing TXA. However, the apparently crystalline features were not observed in sample F2 or sample L, as shown in FIG. 30. Both of these samples were made with 1 mL aqueous TXA.

Example 22—Preparation of Electrospun Mats

Some of the properties of electro spun fibers are their high surface area, inherent 3 dimensional features and tunable porosity. In electro spinning, a thin stream of charged polymer solution is ejected from a spinneret in the presence of a high electric field (in the range of 105 to 106 V/m) applied between a conducting collector and the spinneret. Due to the application of electrostatic potential, the jet will stretch and whip around along with solvent evaporation because of the columbic repulsion between the surface charges. The resulting mass of fine fiber (nanofibers) is then collected on the target electrodes.

This technique can be used to molecules within the fiber matrix. If the drug is soluble in the polymer solution, then the drugs will be homogeneously distributed (dissolved) within the fiber. If, however, the drug particles are not soluble in the polymer matrix, then the insoluble particles will be entrapped within the fiber matrix.

This technique can therefore be used to encapsulate water soluble active pharmaceutical ingredients and/or hemostatic agents (such as, for example tranexamic acid, peptides, proteins) which have poor solubility in organic solvents. Typically, a solution of the organic soluble active pharmaceutical ingredients and/or hemostatic agents with a particle size of less than 100 microns are suspended in an organic solution of a polymer and subjected to the electrospinning process, resulting in matrix of polymer fibers containing particles of drug. This technique is useful since high payloads of drugs can be incorporated into the substrate. The polymer solution may optionally contain other organic soluble compounds, including active pharmaceutical ingredients and/or hemostatic agents. More than one organic insoluble compound can be suspended in the polymer solution.

For example, the organic solution may be mixture of P22-27.5+Rifampin (10% w/w relative to polymer) and Minocycline (10% w/w relative to polymer) dissolved in a 9:1 mixture of THF: Methanol. 10% of fine powder of TXA (10% W/W relative to polymer) may be suspended in this solution and subjected to electrospray. The resulting nanofiber mat would therefore contain 10% each of Rifampin and Minocycline dissolved in the fibers and 10% TXA entrapped between fibers.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An anchorage device configured to surround an implantable medical device, the anchorage device comprising:
a mesh substrate formed from first and second fibers, the first fibers being made of a first material, the second fibers being made of a second material, the second material being different than the first material,
wherein the first material comprises a hemostatic agent,
wherein the second material comprises an active pharmaceutical ingredient,
wherein the hemostatic agent is selected from a group consisting of epinephrine, tranexamic acid and thrombin, and
wherein the substrate is completely biodegradable.

2. An anchorage device as recited in claim 1, wherein the second material is free of any hemostatic agents.

3. An anchorage device as recited in claim 1, wherein the first material consists of the hemostatic agent and the second material consists of the active pharmaceutical ingredient.

4. An anchorage device as recited in claim 3, wherein the substrate consists of the first fibers and the second fibers.

5. An anchorage device as recited in claim 1, wherein the first fibers consist of the first material, the first material consisting of the hemostatic agent, the second fibers consisting of the second material, the second material consisting of the active pharmaceutical ingredient.

6. An anchorage device as recited in claim 5, wherein the substrate consists of the first fibers and the second fibers.

7. An anchorage device as recited in claim 1, wherein the second fibers each consist of the second material, the second material consisting of the active pharmaceutical ingredient.

8. An anchorage device as recited in claim 1, wherein the first fibers consist of the first material, the first material consisting of the hemostatic agent.

9. An anchorage device as recited in claim 1, wherein the active pharmaceutical ingredient comprises a mixture of rifampin and minocycline.

10. An anchorage device as recited in claim 1, wherein the second fibers each consist of the second material, the second material consisting of the active pharmaceutical ingredient, the active pharmaceutical ingredient consisting of rifampin and minocycline.

11. An anchorage device as recited in claim 1, wherein the first fibers each consist of the first material and the second fibers each consist of the second material, the first material consisting of the hemostatic agent and the second material consists of the hemostatic agent and the active pharmaceutical ingredient.

12. An anchorage device as recited in claim 11, wherein the hemostatic agent consists of tranexamic acid and the pharmaceutical ingredient consists of rifampin and minocycline.

13. An anchorage device as recited in claim 12, wherein the substrate consists of the first fibers and the second fibers.

14. An anchorage device as recited in claim 13, wherein the second fibers are interlocked with the first fibers.

15. An anchorage device as recited in claim 13, wherein the first fibers are uniformly spaced apart from one another and the second fibers are uniformly spaced apart from one another.

16. An anchorage device as recited in claim 13, wherein the second fibers each extend transverse to each of the first fibers.

17. An anchorage device as recited in claim 12, wherein the second fibers each extend transverse to each of the first fibers.

18. An anchorage device configured to surround an implantable medical device, the anchorage device comprising:
a mesh substrate consisting of first fibers and second fibers that are interlocked with the first fibers, the first fibers being made entirely from a first material and the second fibers being made entirely from a second material, the second material being different than the first material,
wherein the first material consists of tranexamic acid and the second material is free of any hemostatic agents, the second material comprising a mixture of rifampin and minocycline, and
wherein the substrate is completely biodegradable.

19. An anchorage device as recited in claim 18, wherein the second material consists of the mixture of rifampin and minocycline.

20. An anchorage device configured to surround an implantable medical device, the anchorage device comprising a mesh substrate formed entirely from a plurality of first fibers and a plurality of second fibers that are woven with the first fibers, the first fibers each consisting of tranexamic acid, the second fibers each consisting of rifampin and minocycline, the substrate being completely biodegradable.

* * * * *